(12) United States Patent
Bobra et al.

(10) Patent No.: US 12,150,746 B2
(45) Date of Patent: Nov. 26, 2024

(54) MONITORING A RECEIVER FOR STRIP REPLACEMENT

(71) Applicant: Otsuka Pharmaceutical Co., Ltd., Tokyo (JP)

(72) Inventors: Neraj P. Bobra, San Jose, CA (US); Aditya Dua, San Jose, CA (US); Ronny X. Li, San Francisco, CA (US)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 967 days.

(21) Appl. No.: 17/252,558

(22) PCT Filed: Jun. 14, 2019

(86) PCT No.: PCT/US2019/037257
§ 371 (c)(1),
(2) Date: Dec. 15, 2020

(87) PCT Pub. No.: WO2019/241676
PCT Pub. Date: Dec. 19, 2019

(65) Prior Publication Data
US 2021/0251510 A1     Aug. 19, 2021

Related U.S. Application Data

(60) Provisional application No. 62/685,855, filed on Jun. 15, 2018.

(51) Int. Cl.
*A61B 5/0531*     (2021.01)
*A61B 5/00*     (2006.01)
(Continued)

(52) U.S. Cl.
CPC .......... *A61B 5/0531* (2013.01); *A61B 5/0022* (2013.01); *A61B 5/073* (2013.01);
(Continued)

(58) Field of Classification Search
CPC .......... A61N 1/0492; A61B 2560/0204; A61B 2560/0271; A61B 2560/0214
See application file for complete search history.

(56) References Cited

U.S. PATENT DOCUMENTS 3,876,931 A * 4/1975 Godshalk ............. G01R 31/379
324/429
9,659,423 B2   5/2017 Robertson et al.
(Continued)

FOREIGN PATENT DOCUMENTS

| CN | 101686800 A | 3/2010 |
| CN | 102885615 B | 1/2016 |

(Continued)

OTHER PUBLICATIONS

International Search Report and Written Opinion for International PCT Application No. PCT/US2019/037257, dated Sep. 9, 2019.
(Continued)

*Primary Examiner* — Michael J Dalbo
(74) *Attorney, Agent, or Firm* — Pillsbury Winthrop Shaw Pittman, LLP

(57) ABSTRACT

Systems and methods for monitoring a receiver assembly configured to detect an ingestible event marker signal, the receiver including a disposable component and a reusable component. The methods can include monitoring the skin impedance experienced by the electrodes of the receiver assembly to determine whether the receiver assembly has poor contact quality or is off-body to notify the user accordingly. The methods can also include monitoring a power source level of the receiver assembly, which can be normalized according to the temperature of the receiver assembly, to determine when the power source is at a critical level to notify the user accordingly.

20 Claims, 20 Drawing Sheets

(51) Int. Cl.
*A61B 5/07* (2006.01)
*G16H 40/67* (2018.01)

(52) U.S. Cl.
CPC .......... *A61B 5/6833* (2013.01); *A61B 5/6861* (2013.01); *G16H 40/67* (2018.01); *A61B 2560/0214* (2013.01); *A61B 2560/0271* (2013.01)

(56) References Cited

U.S. PATENT DOCUMENTS

| | | | | |
|---|---|---|---|---|
| 2013/0127611 | A1* | 5/2013 | Bernstein | H01M 10/48 340/455 |
| 2014/0272654 | A1* | 9/2014 | Lebzelter | H01M 8/04253 429/432 |
| 2015/0238094 | A1* | 8/2015 | Lai | A61B 5/0006 600/509 |
| 2017/0056650 | A1 | 3/2017 | Cohen et al. | |

FOREIGN PATENT DOCUMENTS

| | | |
|---|---|---|
| TW | 103109907 A | 2/2015 |
| TW | 202000128 A | 1/2020 |
| WO | 2008095183 A2 | 8/2008 |
| WO | 2010075115 A2 | 7/2010 |
| WO | 2015112603 A1 | 7/2015 |
| WO | 2019241676 A1 | 12/2019 |

OTHER PUBLICATIONS

Office Action issued in related TW Patent Application No. 11220808390, dated Aug. 17, 2023.
Notice of Allowance issued in related TW Patent Application No. 11220808390, dated Jan. 4, 2024.

* cited by examiner

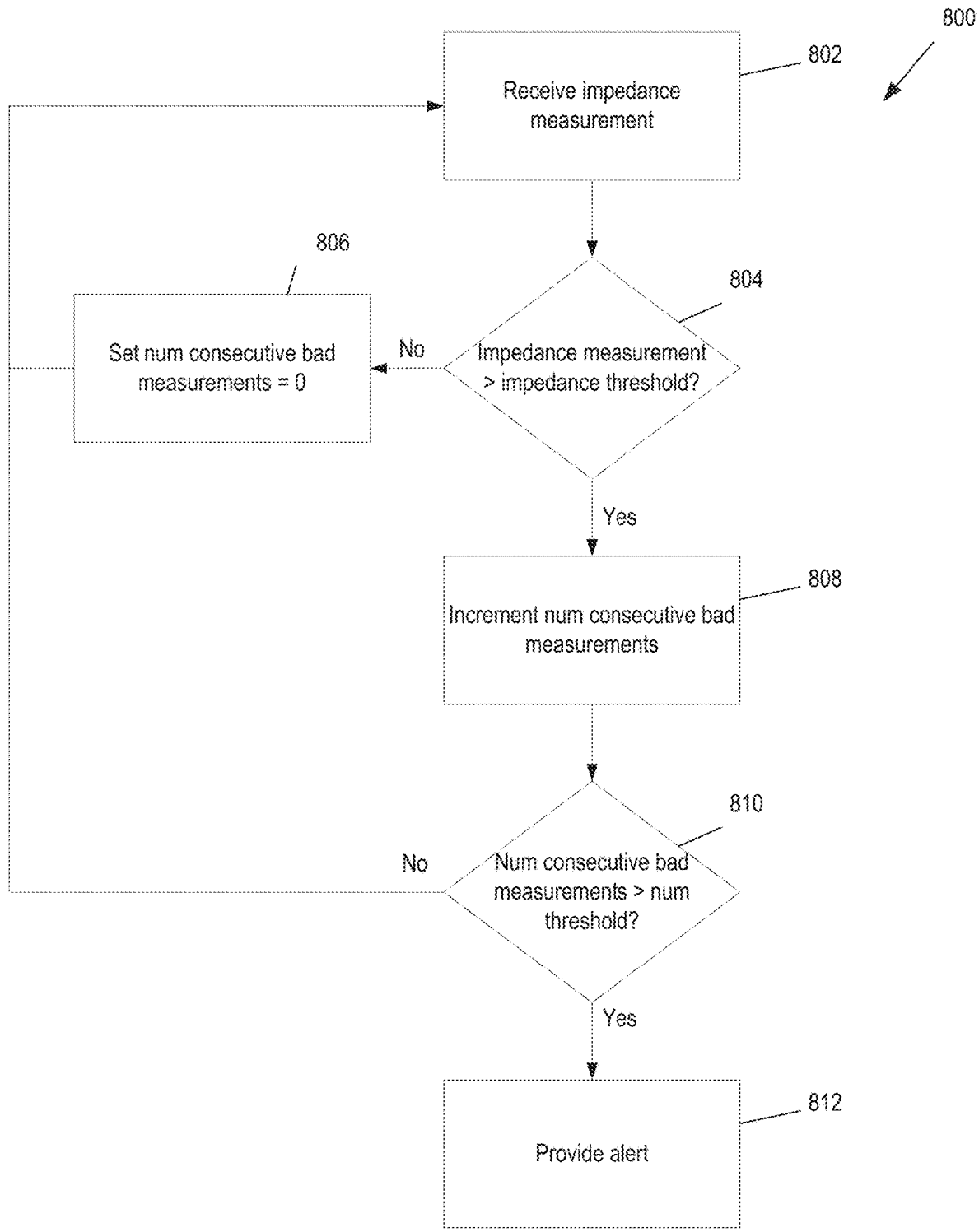

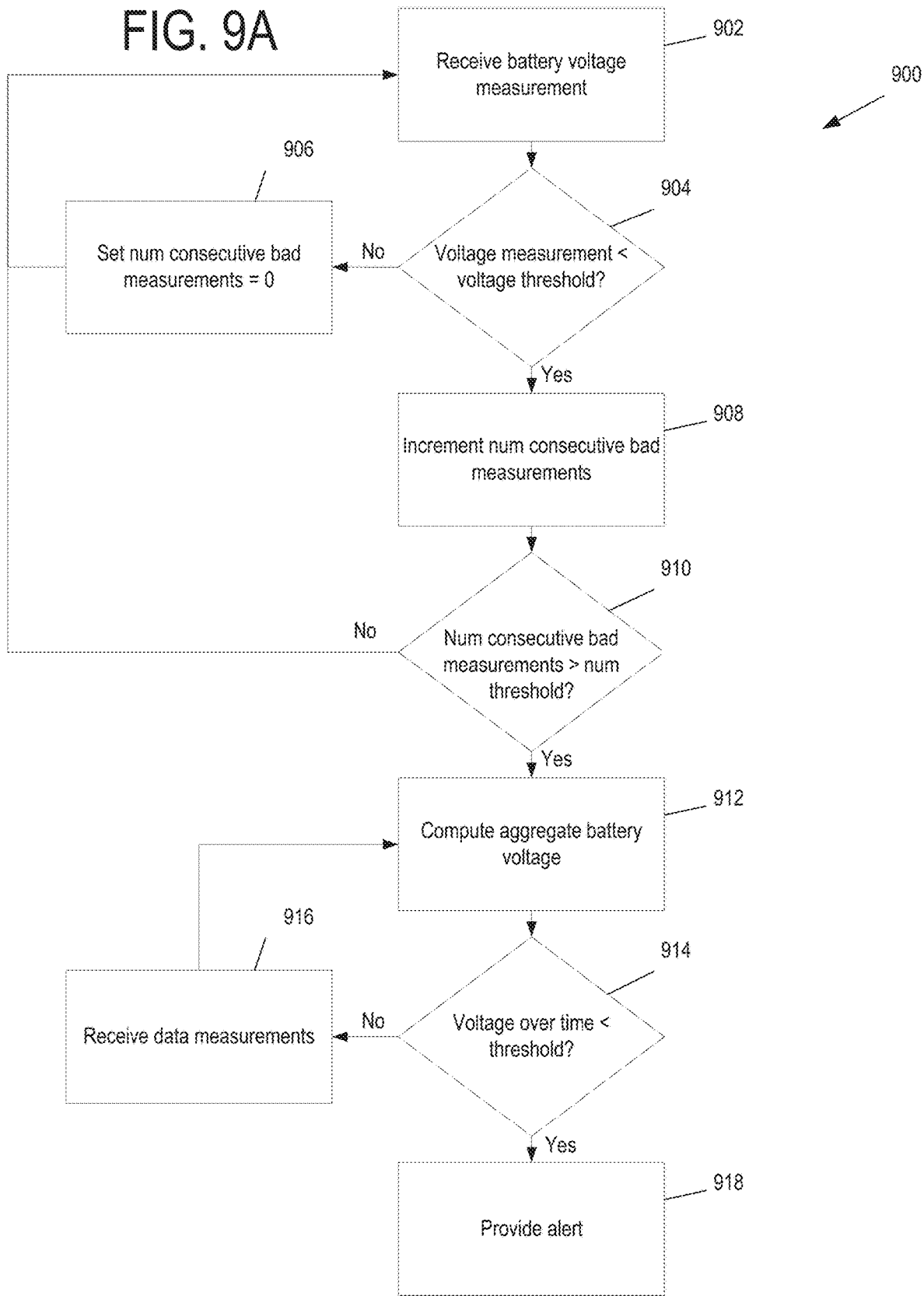

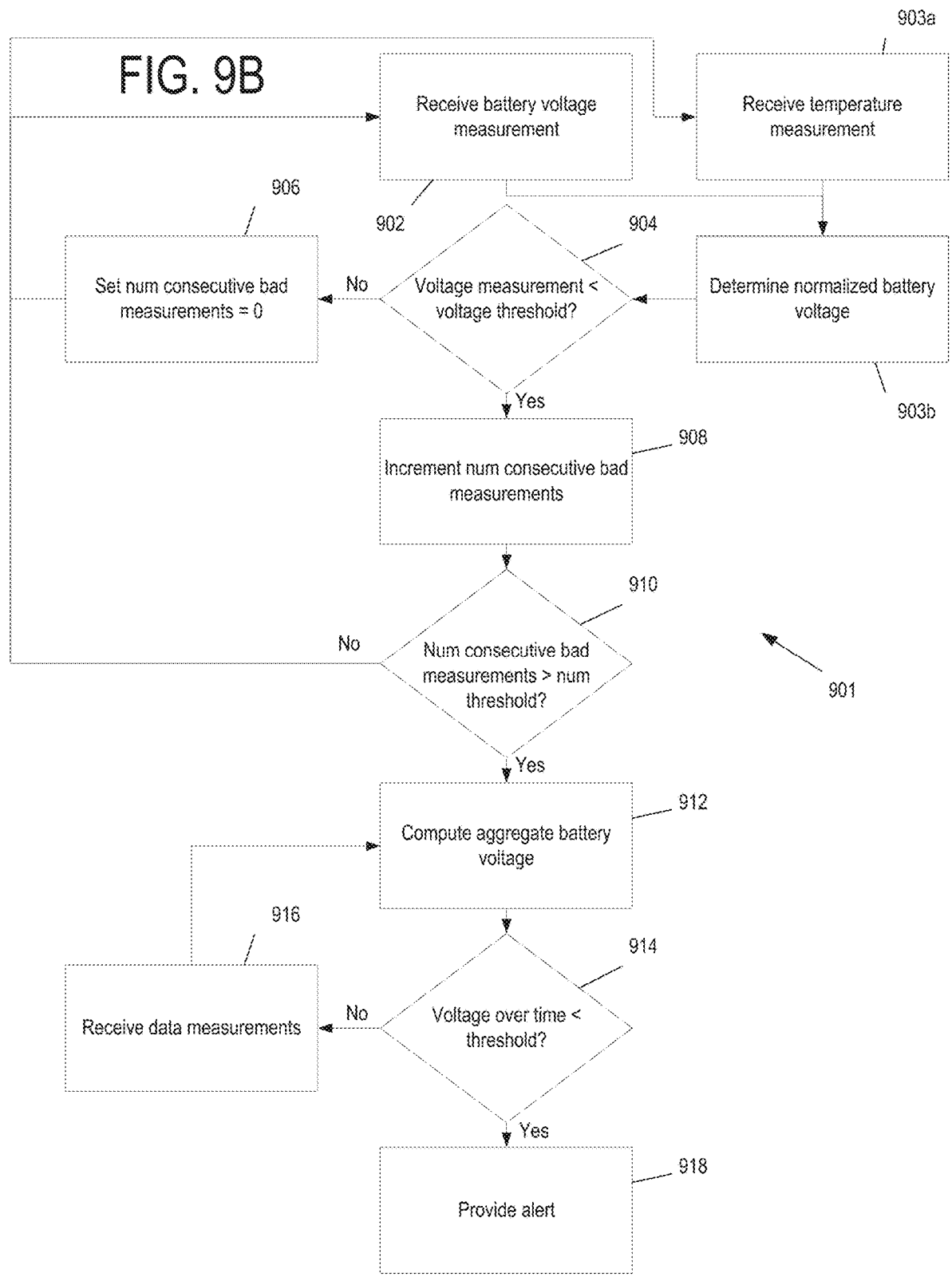

MONITORING A RECEIVER FOR STRIP REPLACEMENT

CROSS-REFERENCE TO RELATED APPLICATIONS

This application is a U.S. National Stage Entry under 35 U.S.C. § 371 of International Patent Application No. PCT/US2019/037257, entitled MONITORING A RECEIVER FOR STRIP REPLACEMENT, filed Jun. 14, 2019, which claims priority to U.S. Provisional Patent Application No. 62/685,855, titled MONITORING A SENSOR ASSEMBLY FOR REPLACEMENT STRIP, filed Jun. 15, 2018, the entire disclosures of which are hereby incorporated by reference herein.

BACKGROUND

Wearable receiver assemblies can be utilized to detect a signal conducted through an individual from an ingestible event marker (IEM). Various embodiments of such receiver assemblies feature a reusable component, which includes the firmware and electronics, and a disposable adhesive strip component, which includes the electrodes and the power source. Because the receiver may not detect the signal from IEM if it has poor contact with the user's skin and/or lacks sufficient power, there is a need for data-driven methods to monitor the condition of the replaceable strip component of such receiver assemblies and correspondingly provide alerts to users to preemptively inform them when the strip component of the receiver assembly needs to be replaced. Further, there is a need for data-driven methods to monitor the replaceable strip component of such receiver assemblies to detect when a patient replaces a used strip component with a new one in order to support troubleshooting in the field and project inventory requirements for a particular patient.

SUMMARY

In one general aspect, a computer-implemented method of monitoring a receiver, wherein the receiver comprises an electrode and is attachable to a body of a user. The method comprises: receiving, by a computer system, a skin impedance measurement of the electrode from the receiver; determining, by the computer system, whether the skin impedance measurement exceeds an impedance threshold; counting, by the computer system, a number of skin impedance measurements that consecutively exceed the impedance threshold; and providing, by the computer system, an alert according to whether the number exceeds a number threshold.

In another general aspect, a device communicably connectable to a receiver, wherein the receiver comprises an electrode and is attachable to a body of a user. The device comprises: a processor; and a memory coupled to the processor, the memory storing instructions that, when executed by the processor, cause the device to: receive a skin impedance measurement of the electrode from the receiver; determine whether the skin impedance measurement exceeds an impedance threshold; count a number of skin impedance measurements that consecutively exceed the impedance threshold; and provide an alert according to whether the number exceeds a number threshold.

In another general aspect, a computer-implemented method of monitoring a receiver, wherein the receiver comprises a power source and an electrode and wherein the receiver is attachable to a body of a user. The method comprises: receiving, by the computer system, a voltage measurement of the power source from the receiver; determining, by the computer system, whether the voltage measurement falls below a voltage threshold; counting, by the computer system, a consecutive number of voltage measurements that fall below the voltage threshold; calculating, by the computer system, an aggregate voltage according to whether the consecutive number of voltage measurements exceeds a threshold; determining, by the computer system, whether the calculated aggregate voltage falls below an aggregate voltage threshold; and providing, by the computer system, an alert according to whether the calculated aggregate voltage falls below the aggregate voltage threshold.

In yet another general aspect, a device communicably connectable to a receiver, wherein the receiver comprises an electrode and a power source and wherein the receiver is attachable to a body of a user. The device comprises: a processor and a memory coupled to the processor, the memory storing instructions that, when executed by the processor, cause the device to: receive a voltage measurement of the power source from the receiver; determine whether the voltage measurement falls below a voltage threshold; count a consecutive number of voltage measurements that fall below the voltage threshold; calculate an aggregate voltage according to whether the consecutive number of voltage measurements exceeds a threshold; determine whether the calculated aggregate voltage falls below an aggregate voltage threshold; and provide an alert according to whether the calculated aggregate voltage falls below the aggregate voltage threshold.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIG. 8 illustrates a logic flow diagram of a process for monitoring a skin impedance of a receiver, in accordance with at least one aspect of the present disclosure.

FIG. 9A illustrates a logic flow diagram of a process for monitoring a battery voltage of a receiver, in accordance with at least one aspect of the present disclosure.

FIG. 9B illustrates a logic flow diagram of a process for monitoring a normalized battery voltage of a receiver, in accordance with at least one aspect of the present disclosure.

DESCRIPTION

Before explaining various aspects of ingestible sensor systems and/or receiver assemblies in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following described aspects, expressions of aspects, and/or examples, can be combined with any one or more of the other following described aspects, expressions of aspects, and/or examples.

Ingestible Sensor Systems

Figure 1:
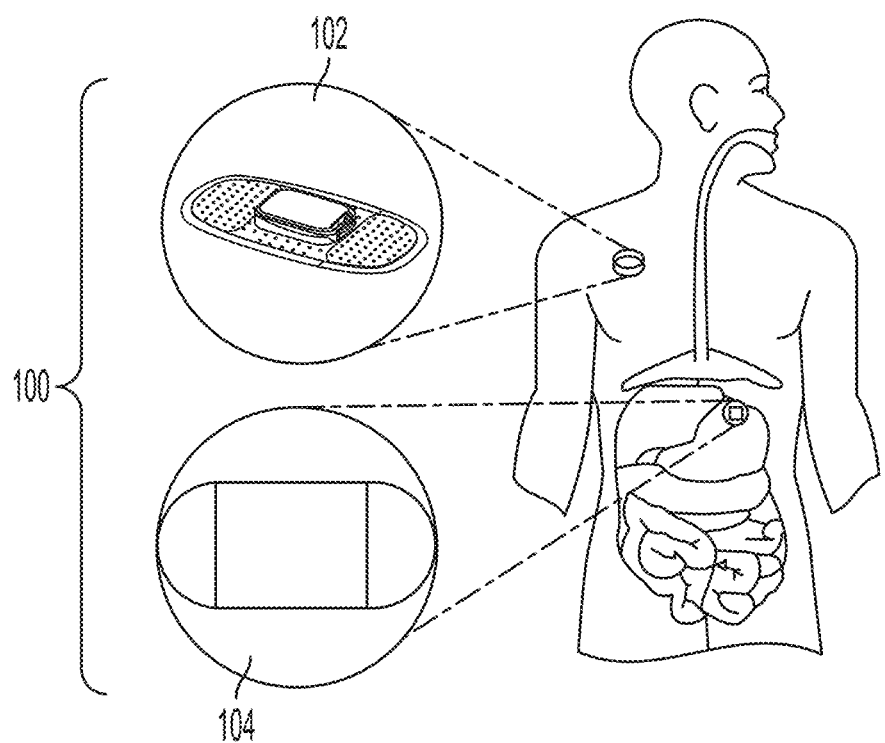
FIG. 1 illustrates a diagram of an ingestible sensor and receiver system, in accordance with at least one aspect of the present disclosure.

FIG. 1 illustrates a diagram of an ingestible sensor and receiver system 100, in accordance with at least one aspect of the present disclosure. The system 100 includes an ingestible sensor or IEM 104 and a receiver 102. The IEM 104 can be incorporated into or present within a physiologically acceptable carrier, such as a pill or other medicament. The IEM 104 can include an embedded, digestible, microchip-based data transmitter. The data transmitter is activated when ingested and sends a unique signal to the receiver 102, which can thus indicate, for example, that the pill or other physiologically acceptable carrier in which the IEM 104 was embedded has been ingested. In the case of multi-drug therapy, each pill ingested by a patient could be embedded or otherwise provided with an IEM 104 configured to emit a unique signal. The microchip can be composed of silicon-based materials that pass easily through the digestive tract and other compounds with a long history of use as vitamins, for example.

The receiver 102 can include a wearable (e.g., as a patch) or subcutaneous implantable receiver that contains a detector to record the ingestion of the IEM 104. In one aspect, the receiver 102 can further include sensors configured to monitor physiological parameters, such as respiration, heart rate, temperature, and/or blood pressure. In one aspect, the receiver 102 can be part of an existing medical implant, such as a pump device, an implantable cardiac defibrillator, a neurological device, and so on. In certain embodiments, the receiver 102 can be configured to store data, such as a patient's medical record.

Figure 7:
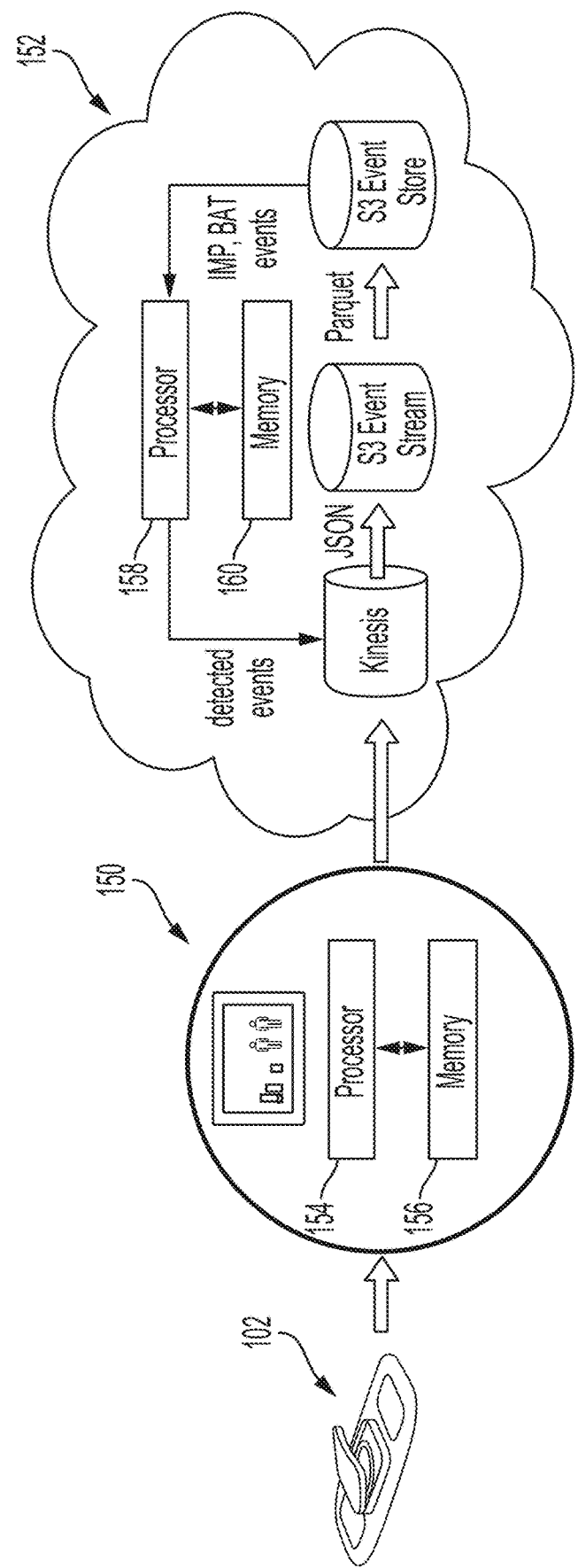
FIG. 7 illustrates a diagram of a system for monitoring a receiver, in accordance with at least one aspect of the present disclosure.

Although not shown in FIG. 1, the system 100 can further include one or more external elements. For example, the receiver 102 can be configured to communicate data to external electronic devices or computer systems, as shown in FIG. 7, for example. Accordingly, the system 100 can allow data gathered on the actual time and level of medication dosing by patients to be integrated with physiologic parameters and presented to patients and physicians in ways that support better individual performance and caregiver clinical decisions and disease management.

Figure 2:
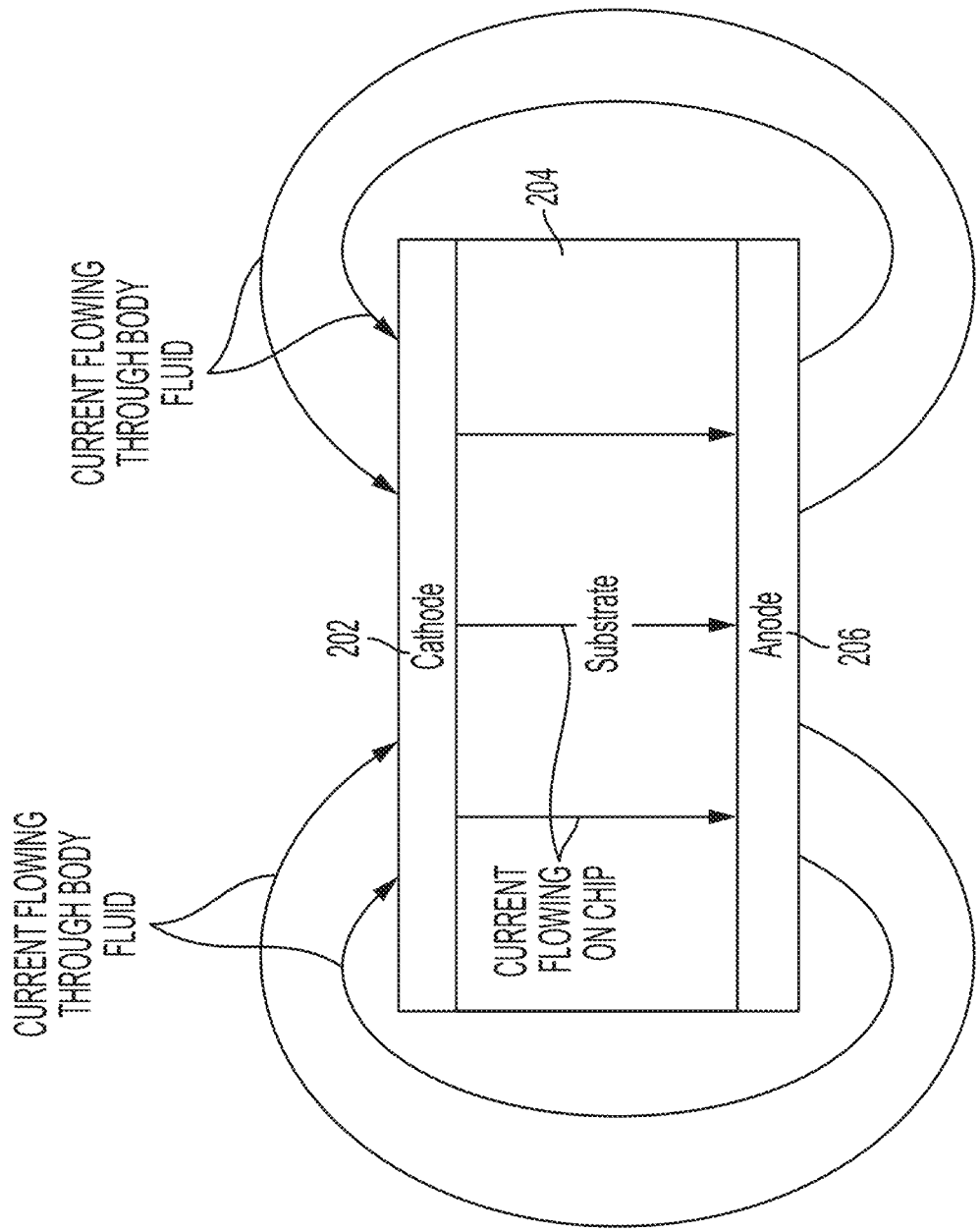
FIG. 2 illustrates a diagram of an IEM, in accordance with at least one aspect of the present disclosure.

FIG. 2 illustrates a diagram of an IEM 104, in accordance with at least one aspect of the present disclosure. In one aspect, the IEM 104 includes a cathode 202 and an anode 206 deposited on a substrate 204 to define a partial voltaic cell or partial power source. The substrate 204 can include an integrated circuit (IC) or chip. The anode 206 can include a layer of magnesium (Mg) and the cathode 202 can include a layer of copper chloride (CuCl), for example. The cathode 202 and anode 206 can form the voltaic cell when in contact with body fluid, which serves as an electrolyte fluid, to power or drive the circuitry of the IEM 104 (which can be fabricated on the substrate 204). The IEM 104 can be configured to change the impedance between the anode 206 and the cathode 202, thereby changing the total amount of current flowing through the body fluid. Further, the IEM 104 can change the rate or manner in which the impedance between the anode 206 and the cathode 202 is changed in order to encode data in the signal defined by the changing electrical current flowing through the body fluid. A receiving circuit, e.g., on a receiver 102, in contact with the body fluid can detect this current change and determine the data encoded in the signal by demodulating the received signal.

Figure 3:
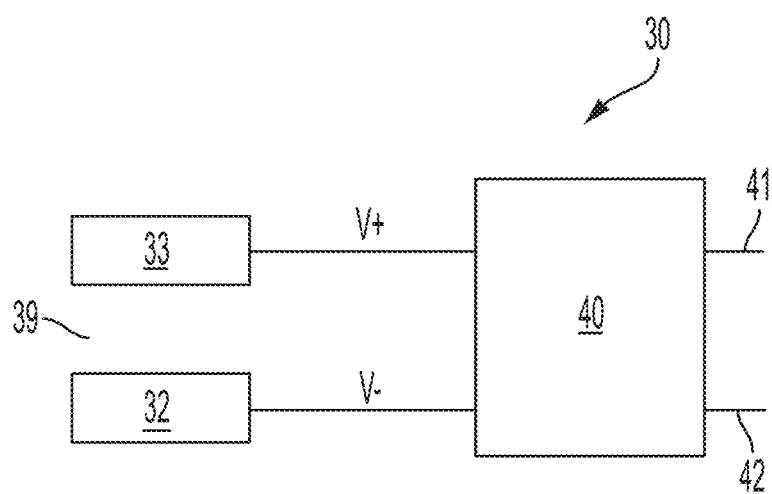
FIG. 3 illustrates a block diagram of a signal generation element of an IEM, in accordance with at least one aspect of the present disclosure.

FIG. 3 illustrates a block diagram of a signal generation element 30 of an IEM 104, in accordance with at least one aspect of the present disclosure. In this example, the signal generation element 30 of the IEM 104 includes a first electrode 32 and a second electrode 33, such as the cathode 202 and the anode 206 illustrated in FIG. 2. When the electrodes 32, 33 are present within an ionic solution 39 (e.g., stomach fluid), they create a low voltage (V−) and a high voltage (V+) as applied to an electronic circuit 40. In this aspect, the electronic circuit 40 is coupled a first output 41 and a second output 42, which can include a first signal-transmission electrode and a second signal-transmission electrode, respectively. In an alternate aspect, the signal generation element 30 can include a single output or signal-transmission electrode. In another alternative aspect, the electrodes 32, 33 can also serve as the signal-transmission electrodes. In an alternative embodiment, a coil for communication may be provided. In certain embodiments, a structure, e.g., membrane, larger than the chip, which defines a path for the current to travel, is provided.

The electrodes 32, 33 can include any two materials appropriate to the environment in which the IEM 104 will be operating. Further, the active materials of the electrodes 32, 33 can include any pair of materials with different electrochemical potentials. For instance, if the ionic solution 39 in which the IEM 104 is to operate is stomach acid, the electrodes 32, 33 can include a noble metal (e.g., gold, silver, platinum, palladium, or the like) so that they do not corrode prematurely. Alternatively, the electrodes 32, 33 can include aluminum or any other conductive material whose survival time in the applicable ionic solution 39 is long enough to allow the IEM 104 to perform its intended function. Suitable materials are not restricted to metals, and in certain aspects, the paired materials are chosen from metals and non-metals, e.g., a pair made up of a metal (e.g., Mg) and a salt (e.g., CuCl). With respect to the active electrode materials, any pairing of substances (metals, salts, or intercalation compounds) with suitably different electrochemical potentials (voltage) and low interfacial resistance are suitable.

Figure 4A:
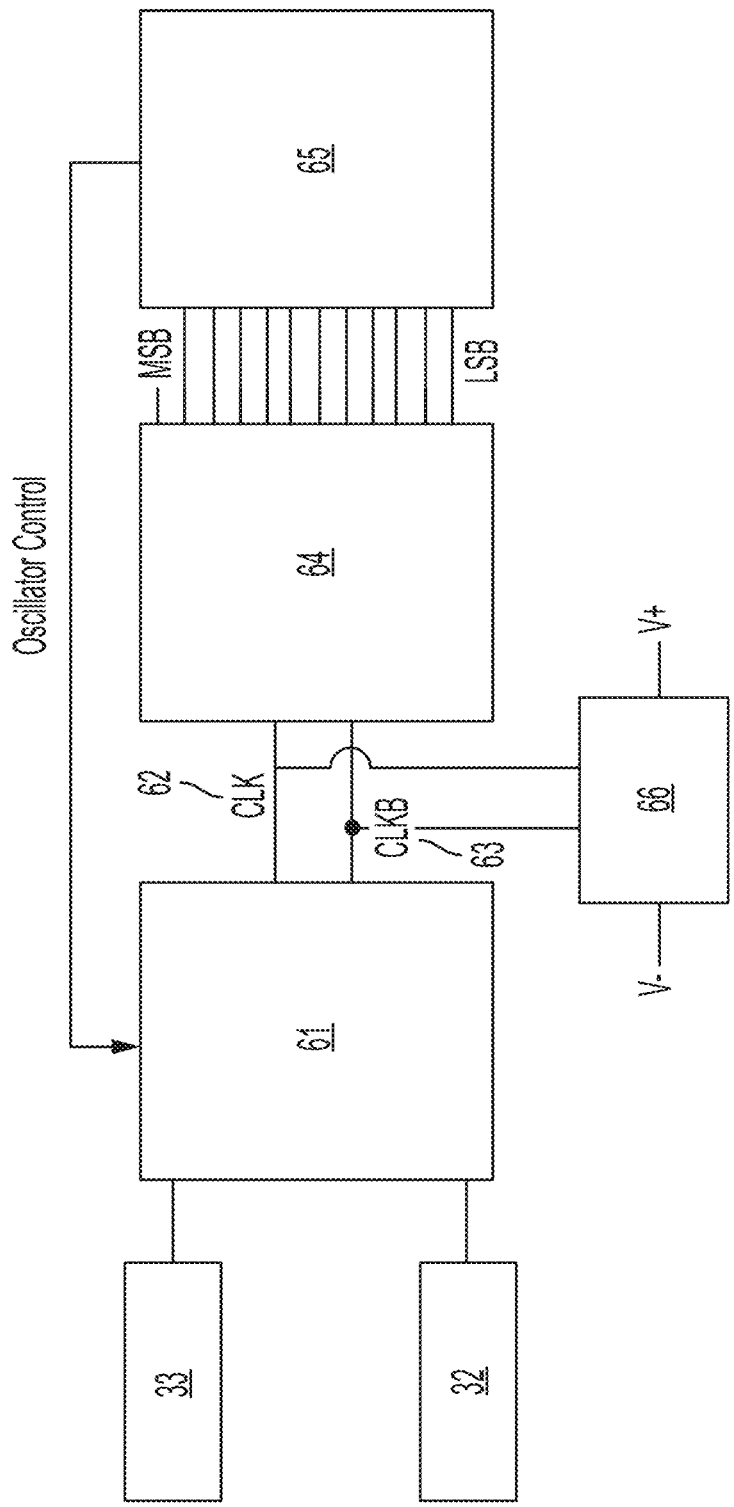
FIG. 4A illustrates a block diagram of an IEM, in accordance with at least one aspect of the present disclosure.

FIG. 4A illustrates a block diagram of an IEM 104, in accordance with at least one aspect of the present disclosure. The IEM circuit can include a pair of electrodes 32, 33 that, when in contract with an electrolyte, form a battery that provides power to an oscillator 61. The first electrode 32 can provides a low voltage (ground) to the oscillator 61. The second electrode 33 can provide a high voltage (V-high) to the oscillator 61. As the oscillator 61 becomes operative due to the provided voltage, it generates a clock signal 62 and an inverted clock signal 63, which are opposites of each other. These two clock signals 62, 63 are fed to the counter 64, which counts the number of clock cycles and stores the count in a number of registers. For example, the counter 64 can include an 8-bit counter. Thus, the output of the counter 64 begins with a value of "00000000," changes to a value of "00000001" at the first clock cycle, and continues until it reaches an output value of "11111111." The 8-bit output of counter 64 is coupled to the input of an address multiplexer (mux) 65. In one embodiment, the mux 65 includes an address interpreter, which can be hard-wired in the circuit, and generates a control voltage to control the oscillator 61. The mux uses the output of the counter 64 to reproduce the address in a serial bit stream, which is further fed to the signal-transmission driving circuit. The mux 65 can also be used to control the duty cycle of the signal transmission. In one embodiment, the mux 65 activates signal transmission only one-sixteenth of the time, using the clock counts generated by the counter 64. Such a low-duty cycle conserves power and also allows other devices to transmit without jamming their signals. The address of a given chip can be 8 bits, 16 bits, or 32 bits, in various aspects.

In one aspect, the mux 65 produces a control voltage, which encodes the address serially and is used to vary the output frequency of the oscillator 61. For example, when the control voltage is low, that is, when the serial address bit is at a 0, a 1 megahertz signal can be generated by the oscillator 61. When the control voltage is high, that is, when the address bit is a 1, a 2 megahertz signal can be generated the oscillator 61. In other examples, the oscillator 61 can be configured to generate 10 megahertz and 20 megahertz signals or can be configured to generate a phase shift keyed signal. In other words, the mux 65 controls the frequency of the oscillator 61 or an AC alternative embodiment of the amplified signal of oscillation.

The outputs of the mux 65 are coupled to an electrode drive 66, which can drive the electrodes to impose a differential potential to the solution, drive an oscillating current through a coil to generate a magnetic signal, or drive a single electrode to push or pull charge to or from the solution. In this manner, the IEM circuit can broadcast the sequence of 0s and 1s that define the address stored in the mux 65. That address could be broadcast repeatedly until, for example, one of the electrodes 32, 33 is consumed and dissolved in the ionic solution 39 (i.e., when the voltaic cell is no longer operable).

Figure 4B:
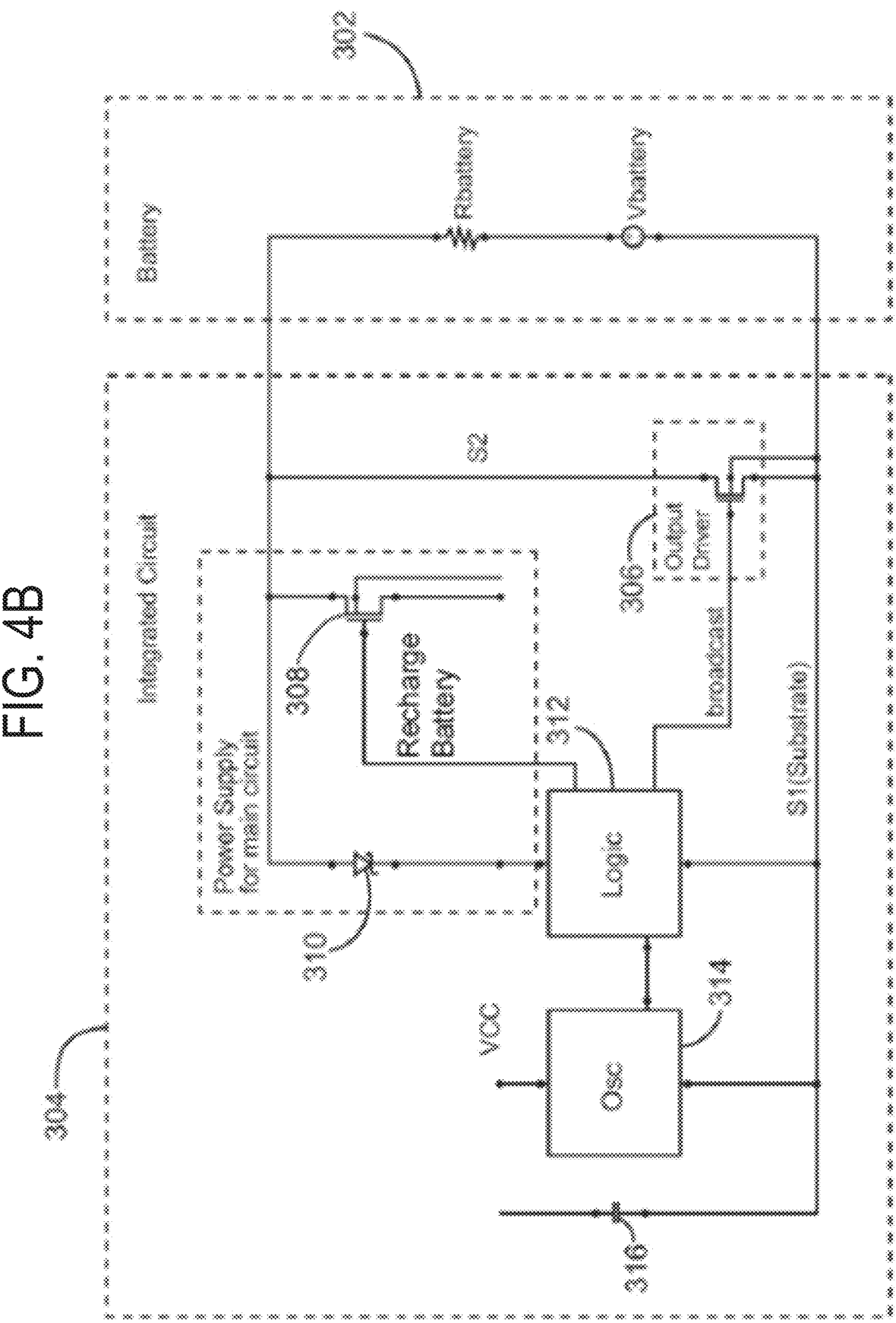
FIG. 4B illustrates a block diagram of an IEM, in accordance with at least one aspect of the present disclosure.

FIG. 4B illustrates a block diagram of an IEM 104, in accordance with at least one aspect of the present disclosure. In one aspect, the IEM 104 can include a battery section 302 and an integrated circuit 304. Battery section 302 includes the voltaic cell electrodes (e.g., the electrodes 32, 33 in FIGS. 3 and 4A and/or the anode 206 and cathode 202 in FIG. 2), which, when coupled with an electrolyte fluid, form a voltaic cell. The two battery electrodes are coupled to the high-voltage rail (VCC) and ground for the IC circuitry, respectively. The IC circuitry 304 includes a transmission switch transistor 306, a recharge transistor 308, a recharge-protection diode 310, a recharge capacitor 316, a local oscillator 314 (e.g., the oscillator 61 in FIG. 4A), and a control logic 312. The local oscillator 314 produces one or more carrier frequencies that is used by control logic 312 to issue a transmission command (labeled as "broadcast") to turn on and off transmission switch transistor 306. For example, the local oscillator 314 can produce a 20 KHz signal, based on which control logic 312 can generate a binary-phase shift keying (BPSK)-encoded message. The control logic 312 then switches on and off transmission switch transistor 306 to transmit these messages.

When the transmission switch transistor 306 is turned on by the control logic 312, a low-impedance external return circuit is provided between the two voltaic-cell electrodes. Consequently, the current flowing through the patient's body is also increased. When the transmission switch transistor 306 is turned off by the control logic 312, the external return circuit between the two voltaic-cell electrodes exhibits a high impedance. Correspondingly, the current When the transmission switch transistor 306 is turned on, the two voltaic-cell electrodes are effectively shorted. As a result, the voltage provided by the electrodes is significantly lower than when transmission switch transistor 306 is turned off. To ensure that the control logic 312 continues to operate properly, the recharge capacitor 316 provides the necessary voltage (VCC) to the control logic 312. Note that the recharge capacitor 316 is recharged when the IEM chip is in a silence period, i.e., when the transmission switch transistor 306 remains off. When the transmission switch transistor 306 turns on (which causes the voltage between the battery electrodes to drop), the recharge-protection diode 310 prevents the charge stored in recharge capacitor 316 from flowing back to the battery electrodes. The recharge-protection diode 310 can include a Schottky diode to ensure a fast switching time, flowing through the patient's body is significantly lower. Note that the current draw of the rest of the circuitry, e.g., the local oscillator 314 and control logic 312, is sufficiently low so that there is a significant difference in the body current between the broadcast period and the silence period.

It is possible that, during the transmission period, local oscillator 314 and/or control logic 312 have depleted the charges stored in the recharge capacitor 316, causing VCC to drop below a certain threshold. For example, the voltage provided by the recharge capacitor 316 may drop below the voltage provided by the voltaic cell. The difference between these two voltages may not be large enough to turn on the recharge-protection diode 310. In this case, the control logic 312 can issue a recharge signal to turn on recharge transistor 308, which couples the battery voltage to the recharge capacitor 316 and recharges the recharge capacitor 316.

In various aspects, the components or functional blocks of the IEM circuitry can be present on integrated circuits, where the integrated circuits include a number of distinct functional blocks, i.e., modules. Within a given IEM circuit, at least some of (e.g., two or more, up to an including all of) the functional blocks (e.g., the power source and/or transmitter), may be present in a single integrated circuit or circuit structure. As such, the integrated circuit can be a monolithic integrated circuit (also known as a microcircuit, microchip, silicon chip, computer chip, or chip) that is a miniaturized electronic circuit (which may include semiconductor devices, as well as passive components) that has been manufactured in or on the surface of a thin substrate of semiconductor material. The integrated circuits of certain aspects may be hybrid integrated circuits, which are miniaturized electronic circuits constructed of individual semiconductor devices, as well as passive components, bonded to a substrate or circuit board.

Additional details regarding the IEM structure and signal processing techniques for transmitting, receiving, and analyzing IEM signals can be found in U.S. Pat. No. 8,858,432, titled INGESTIBLE EVENT MARKER SYSTEMS, which is hereby incorporated by reference in its entirety.

Receiver Systems

Figure 5:
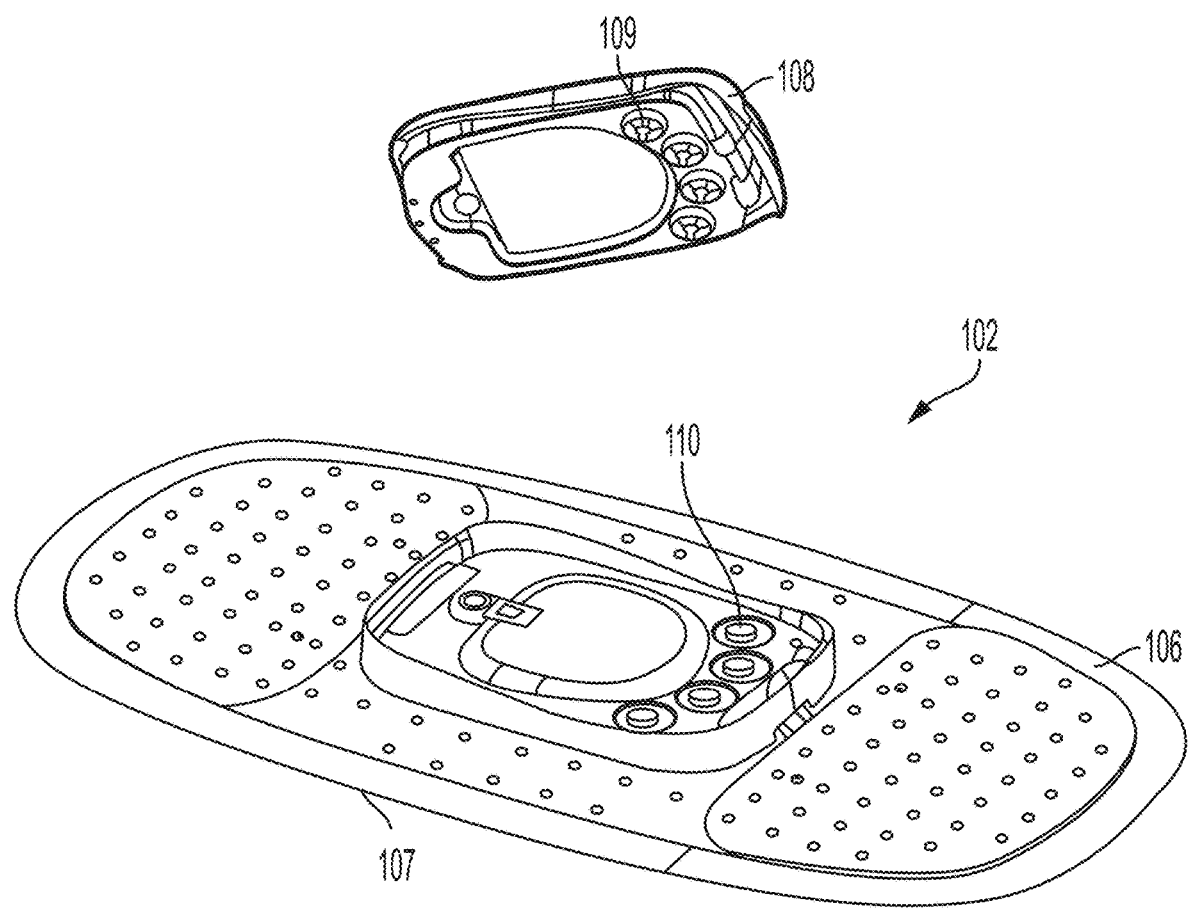
FIG. 5 illustrates an exploded view of a receiver, in accordance with at least one aspect of the present disclosure.

As noted above, the system 100 can include a receiver 102 that is configured to receive signals generated by the IEM 104. In various aspects, the receiver 102 can include disposable and reusable components that are removably affixable together. In one aspect illustrated in FIG. 5, the receiver 102 can include a strip 106 that is attachable to a body of a user for receiving the IEM signals and detecting other data. The strip 106 can be attachable to a body via an adhesive surface 107, for example. The strip 106 can include electrodes 112 (FIGS. 6A, 6B) positioned along or adjacent to the adhesive surface 107 that is securable to the user's body in order to position the electrodes 112 thereagainst for receiving IEM signals and detecting other data. The strip 106 can further be configured to removably receive a control module 108 (or "pod") containing circuitry and/or electronics for processing received IEM signals, receiving data from the strip 106, and/or transmitting data to external systems. The control module 108 can include contacts 109 that are configured to cooperate with corresponding contacts 110 disposed on the strip 106 for communicating electrical signals received via the electrodes 112 of the strip 106 to the control module 108. Because the control module 108 is reversibly connected to the strip 106, the control module 108 can be reused when the strip 106 is replaced (e.g., because the adhesive surface 107 has begun to fail). The strip 106 can be a disposable component, and the control module 108 can be a reusable component.

Figure 6A:
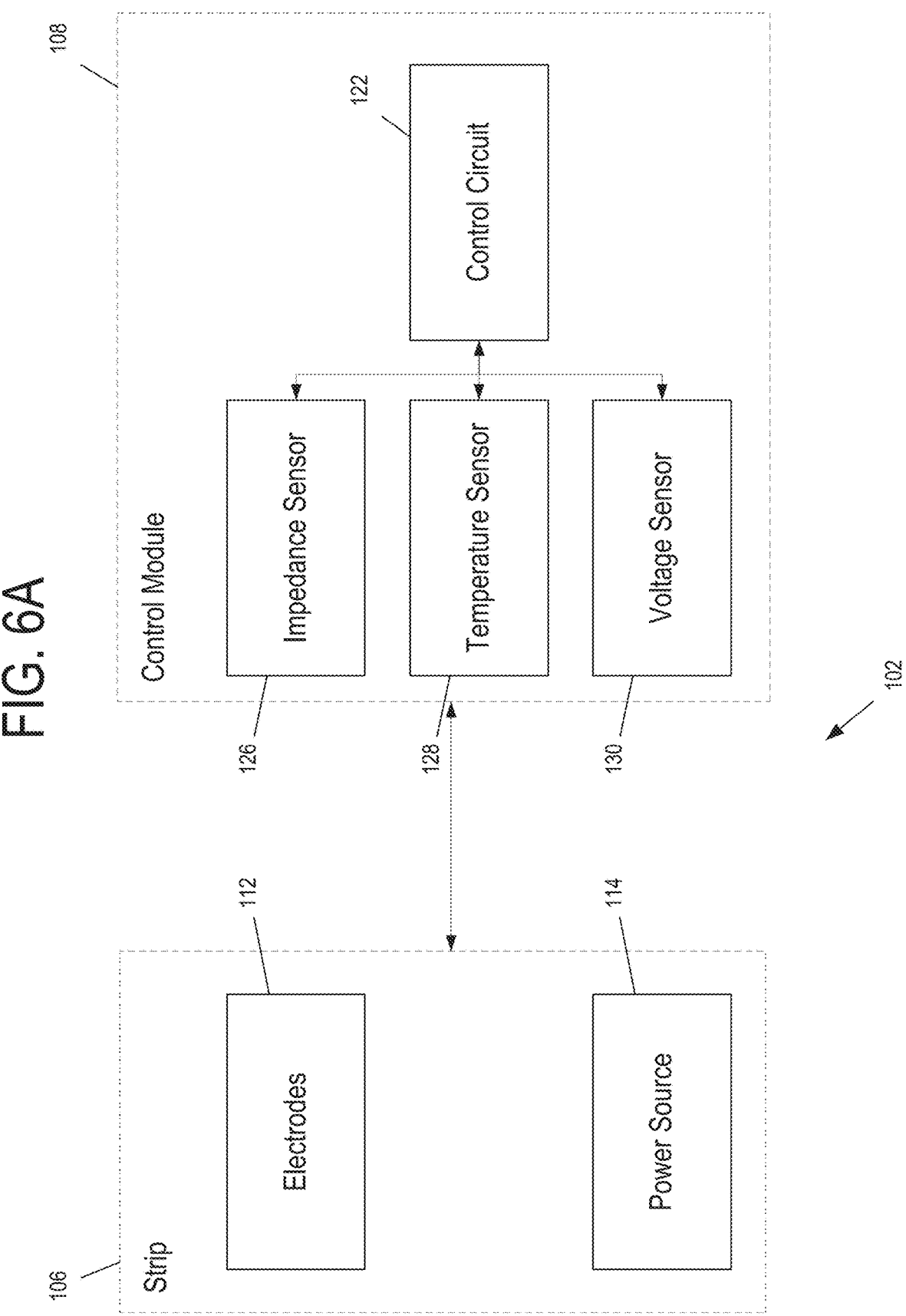
FIG. 6A illustrates a first block diagram of a receiver, in accordance with at least one aspect of the present disclosure.
Figure 6B:
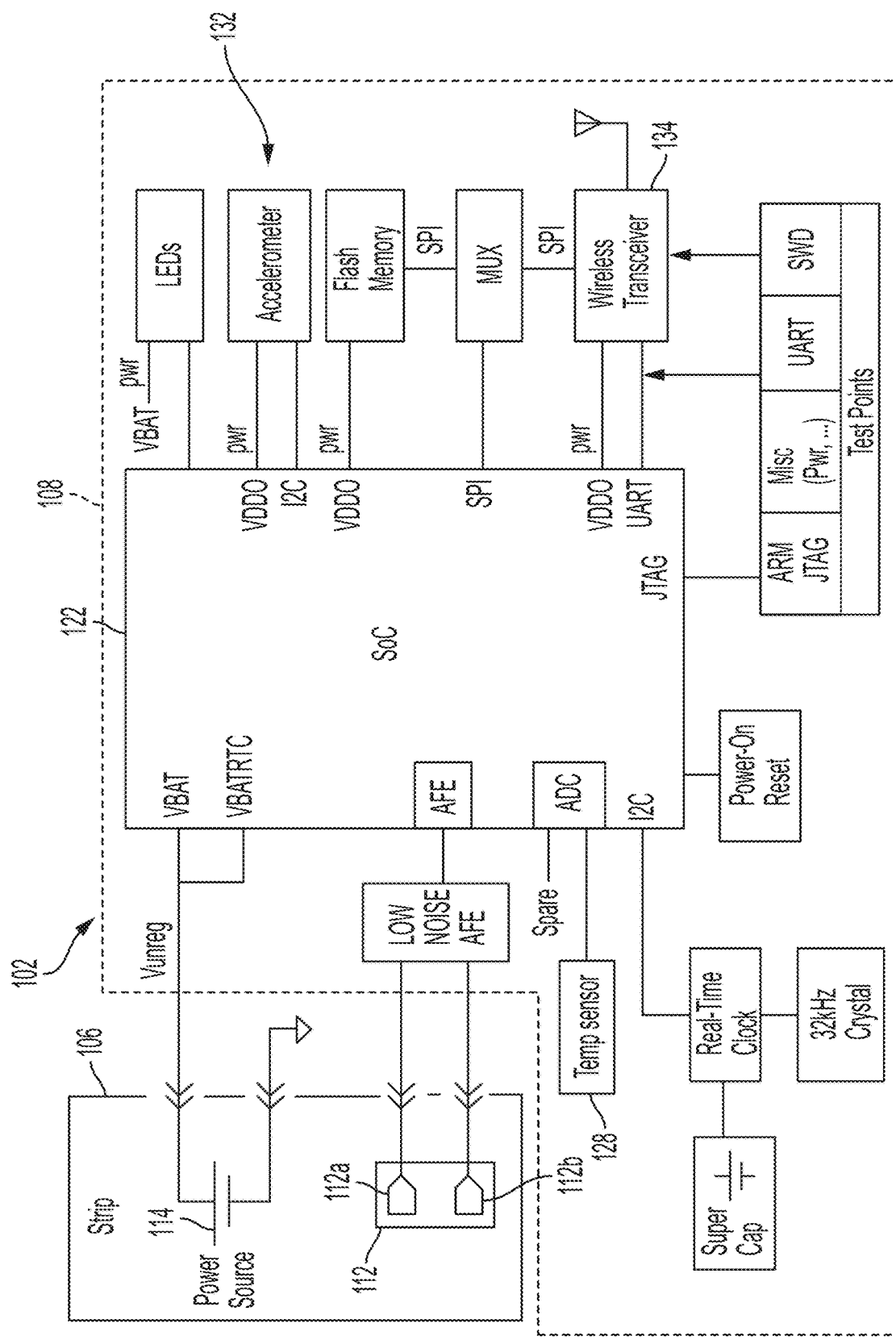
FIG. 6B illustrates a second block diagram of a receiver, in accordance with at least one aspect of the present disclosure.

FIG. 6A illustrates a first block diagram of the receiver 102. Reference should also be made to FIG. 6B, which illustrates a second and/or alternative block diagram of the receiver 102. The adhesive strip 106 includes electrodes 112 (e.g., a first electrode 112a and a second electrode 112b) and a power source 114 for powering the electrodes 112. The power source 114 can include a battery, such as a 3V lithium coin cell battery. In one aspect, the electrodes 112 and the power source 114 can be supported upon a substrate, such as a PCBA. As noted above, the strip 106 can be secured to a subject, and the electrodes 112 can be arranged such that they contact the skin of the subject when the strip 106 is secured to the subject. When contacting the skin of a subject, the electrodes 112 are configured to receive a signal from an ingestible sensor, such as an IEM 104 described above under the heading INGESTIBLE SENSOR SYSTEMS. When the control module 108 is secured to the adhesive strip 106, the control module 108 is communicably coupled to the electrodes 112 and other components of the adhesive strip 106 via, for example, the cooperating contacts 109, 110 disposed on the control module 108 and the adhesive strip 106. The control module 108 includes the firmware and various electronics for processing the signal received from the IEM 104.

In one aspect, the receiver 102 can further include an impedance sensor 126 configured to measure the impedance at or experienced by the electrodes 112. In another aspect, the receiver 102 can further include a voltage sensor 130 configured to measure the voltage of the power source 114. In another aspect, the receiver 102 can further include a temperature sensor 128 configured to measure the temperature of the strip 106 or a component thereof. For example, the temperature sensor 128 can be configured to measure the temperature of the PCBA or substrate supporting the components of the strip 106. In the depicted aspect, the impedance sensor 126, voltage sensor 130, and temperature sensor 128 are disposed in or on the control module 108. In other aspects, one or more of the impedance sensor 126, voltage sensor 130, and/or temperature sensor 128 can be disposed in or on the strip 106 (e.g., supported upon the PCBA) or otherwise be separate from the control module 108 and/or strip 106. In aspects where the impedance sensor 126 is a component of the control module 108, the impedance sensor 126 can be communicatively coupled via the contacts 109, 110 to the electrodes 112 when the control module is connected to the adhesive strip 106. Likewise, in aspects where the voltage sensor 130 is a component of the control module 108, the voltage sensor 130 can be communicatively coupled via the contacts 109, 110 to the power source 114 when the control module 108 is connected to the adhesive strip 106. In one aspect, the receiver 102 can include a variety of other sensors for sensing parameters associated with the wearer of the receiver 102 and/or the receiver 102 itself. For example, the aspect depicted in FIG. 6B further includes an accelerometer 132 for detecting the orientation and/or movement of the control module 108.

In one aspect, the receiver 102 can include a control circuit 122 that is configured to receive and demodulate signals received from the IEM 104, communicate data to external sources, and/or execute one or more processes for monitoring one or more states or parameters associated with the adhesive strip 106. The control circuit 122 includes, for example, a processor executing instructions stored from a memory, an application-specific integrated circuit (ASIC), a system-on-a-chip (SoC) (as in the aspect depicted in FIG. 6B), a field-programmable gate array (FPGA), firmware, and combinations thereof.

In one aspect, the receiver 102 can further include a transceiver for sending data to and receiving data from external systems. For example, in the aspect illustrated in FIG. 6B, the control module 108 includes a wireless transceiver 134, such as a Bluetooth Low Energy (BLE) transceiver. The transceiver can be utilized to transmit detection events and other data associated with IEMs, sensor data associated with the wearer of the receiver 102 or the receiver 102 itself, and other data to external computer systems, such as a back-end computer system 152 (FIG. 7).

FIG. 7 illustrates a system for monitoring a receiver 102. In one aspect, the receiver 102 can be communicably connectable to a mobile device 150 (e.g., a smartphone or tablet) and/or a back-end computer system 152. In one aspect, the mobile device 150 can be paired with or communicably coupled to the receiver 102 such that the receiver 102 provides data sensed by the receiver 102 to the mobile device 150 for analysis by an app being executed thereon. The receiver 102 can be communicably coupled to the mobile device 150 via, for example, a BLE connection for pairing the mobile device 150 and the receiver 102.

The mobile device 150 can include a memory 156 and a processor 154 coupled to the memory 156 for executing instructions stored therein. The back-end computer system 152 can include a cloud computing architecture, for example. The back-end computer system 152 can include a memory 160 and a processor 158 coupled to the memory 160 for executing instructions stored therein. In the aspect depicted in FIG. 7, the receiver 102 is configured to transmit data (e.g., receiver sensor data) via the wireless transceiver 134 (FIG. 6B) to a local mobile device 150 paired to or otherwise coupled with the receiver 102, which is then in turn configured to transmit the data to the back-end computer system 152. In other aspects, the receiver 102 can be configured to directly transmit or upload data to the back-end computer system 152. The back-end computer system 152 is configured to receive data at a real-time data streaming service (e.g., Kinesis) and then store the received data in one or more databases in various data storage formats (e.g., JavaScript Object Notation (JVON) or Apache Parquet). The back-end computer system 152 can further be configured to execute various algorithms on the received data (e.g., impedance events/measurements or battery events/measurements) to determine whether various events have occurred, whether alerts should be provided to the user, and so on. Based on these algorithms, the back-end computer system 152 can push or transmit alerts or data (e.g., the occurrence of a strip change) to the mobile device 150 for viewing by the user (e.g., via an app).

Various processes are discussed below by way of logic flow diagrams. For brevity, the following processes are discussed as being executed by a control circuit; however, it should be understood that a control circuit encompasses a variety of different combinations of hardware and software and, accordingly, the described processes can be executed by the processor 154 of the mobile device 150, the processor 158 of the back-end computer system 152, the control circuit 122 of the control module 108, and so on. In other words, the described processes can be executed by the mobile device 150, the back-end computer system 152, the receiver 102, and other computing systems. For example, the processes can be embodied as a set of instructions stored in the memory 156 of the device 150 that, when executed by the processor 154, cause the mobile device 150 to perform the enumerated steps.

Strip Change Monitoring

FIG. 8 illustrates a logic flow diagram of a process 800 for monitoring a skin impedance of a receiver 102, in accordance with at least one aspect of the presence disclosure. In the following description of the process, reference should also be made to FIGS. 1 and 6A-7. The illustrated process can be executed by, for example, a control circuit. The skin impedance of the receiver 102 can be indicative of the contact quality between the electrodes 112 of the receiver 102 and the user's skin, which is important for a number of different reasons. For example, poor contact quality can inhibit the ability of the receiver 102 to detect and demodulate a signal being transmitted by an IEM 104. As another example, a high impedance experienced by the receiver 102 can indicate that the receiver 102 has become detached from the user's body and would thus be unable detect the signal from the IEM 104 and/or capture other sensor data.

Accordingly, the control circuit receives 802 impedance measurements from the impedance sensor 126 coupled to the electrodes 112 of the receiver 102. The impedance at the electrodes 112 can indicate the quality of the contact between the electrodes 112 and the skin of the user. Impedance measurements, for example, between 500-4,000 ohms or 500-7,000 ohms can be characterized as or indicate good contact between the electrodes 112 and the skin of the user. Impedance measurements, for example, greater than 10,000 ohms can be characterized as or indicate poor contact between the electrodes 112 and the skin of the user. Impedance measurements, for example, greater than or equal to 20,000 ohms can indicate that the receiver 102 is off-body (i.e., not in contact with the skin of the user).

In one aspect, the impedance can be measured at a fixed interval. In another aspect, the impedance can be measured at variable intervals. In this aspect, the interval at which the impedance is measured can be varied according to, for example, the state of the receiver 102 and/or in relation to other events. In one aspect, the impedance can be measured at a first interval (e.g., 30 seconds) during a time period (e.g., 20 minutes) after the control module 108 has been rebooted and a second interval (e.g., 20 minutes) thereafter. The control module 108 can be configured to reboot when, for example, first connected to or inserted in a strip 106.

Accordingly, the control circuit determines the value of the impedance measurement relative to a first or impedance threshold. In one aspect, the control circuit determines 804 whether the impedance measurement is greater than an impedance threshold. The impedance threshold can be set to a value corresponding to different events or states that are desired to be monitored. For example, if it is desired to monitor whether there is poor skin contact with the electrodes 112, the impedance threshold can be set to, e.g., 10,000 ohms. As another example, if it is desired to monitor whether the receiver 102 is off-body, the impedance threshold can be set to, e.g., 20,000 ohms.

The process 800 executed by the control circuit can be programmed to track the number of consecutive "bad" impedance measurement readings. In one aspect, the process 800 is configured to track the number of impedance readings that exceed a predetermined threshold. For example, if the impedance measurement is not above the threshold, then the process 800 proceeds along the NO branch and the control circuit sets 806 a counter tracking the number of consecutive impedance measurements that exceed the impedance threshold to zero. The control circuit then continues receiving 802 impedance measurements from the impedance sensor 126 coupled to the electrodes 112. Conversely, if the impedance measurement is determined 804 to be above the threshold, then the process 800 proceeds along the YES branch and the control circuit increments 808 the counter tracking the number of consecutive impedance measurements that exceed the impedance threshold. Accordingly, the control circuit determines 810 whether the number of consecutive impedance measurements exceeds a second threshold. If the number of consecutive measurements is not above the second threshold, then the process 800 proceeds along the NO branch and the control circuit continues receiving 802 impedance measurements from the impedance sensor 126 coupled to the electrodes 112. If the number of consecutive measurements is above the second threshold, then the process 800 proceeds along the YES branch and the control circuit can initiate an action in response. In the aspect depicted in FIG. 8, the control circuit provides 812 an alert, such as by causing a push notification to be generated at the user's mobile device 150. In other aspects, the control circuit can generate a signal that is transmitted to a secondary computer system, deactivate the sensor assembly, and/or take a variety of other actions.

In sum, the process 800 illustrated in FIG. 8 allows the system 100 to monitor contact quality of the electrodes 112 to the user so that users can take corrective action, such as reattaching the receiver 102 or replacing the adhesive strip 106, in instances where the contact quality of the electrodes 112 is poor. Further, because impedance measurements at the electrodes can be noisy, the process 800 mitigates the occurrence of false positive detection events by only initiating an action (e.g., providing an alert) if there has been at least a threshold consecutive number of instances where the measured impedance has exceeded the threshold. Providing users with the ability to take corrective action is important because it avoids detection failure of IEM signals and receiver sensor data.

FIGS. 9A and 9B illustrate logic flow diagrams of processes 900, 901 for monitoring a battery voltage of a receiver 102, in accordance with at least one aspect of the present disclosure. As will be discussed in greater detail below, the processes 900, 901 differ in that the process 900 in FIG. 9A monitors unnormalized voltage measurements and the process 901 in FIG. 9B monitors temperature-normalized voltage measurements. In the following description of the processes 900, 901, reference should also be made to FIGS. 1 and 6A-7. The illustrated processes 900, 901 can be executed by, for example, a control circuit.

Accordingly, the control circuit receives 902 voltage measurements from the power source 114 of the strip 106 via the voltage sensor 130. In aspects where the power source 114 is a battery, the control circuit thus receives battery voltage measurements. The battery voltage measurements can include, for example, loaded and/or unloaded battery voltage. An unloaded battery can, in some circumstances, provide a more stable voltage measurement than other voltage measurements of the battery. In some aspects, the control circuit additionally receives equivalent series resistance (ESR) measurements. ESR can be calculated by the control circuit according to, for example, the difference between the loaded and unloaded battery voltages divided by the input current (e.g., 7 mA). As battery life decreases, battery voltage decreases and ESR increases.

Figure 13:
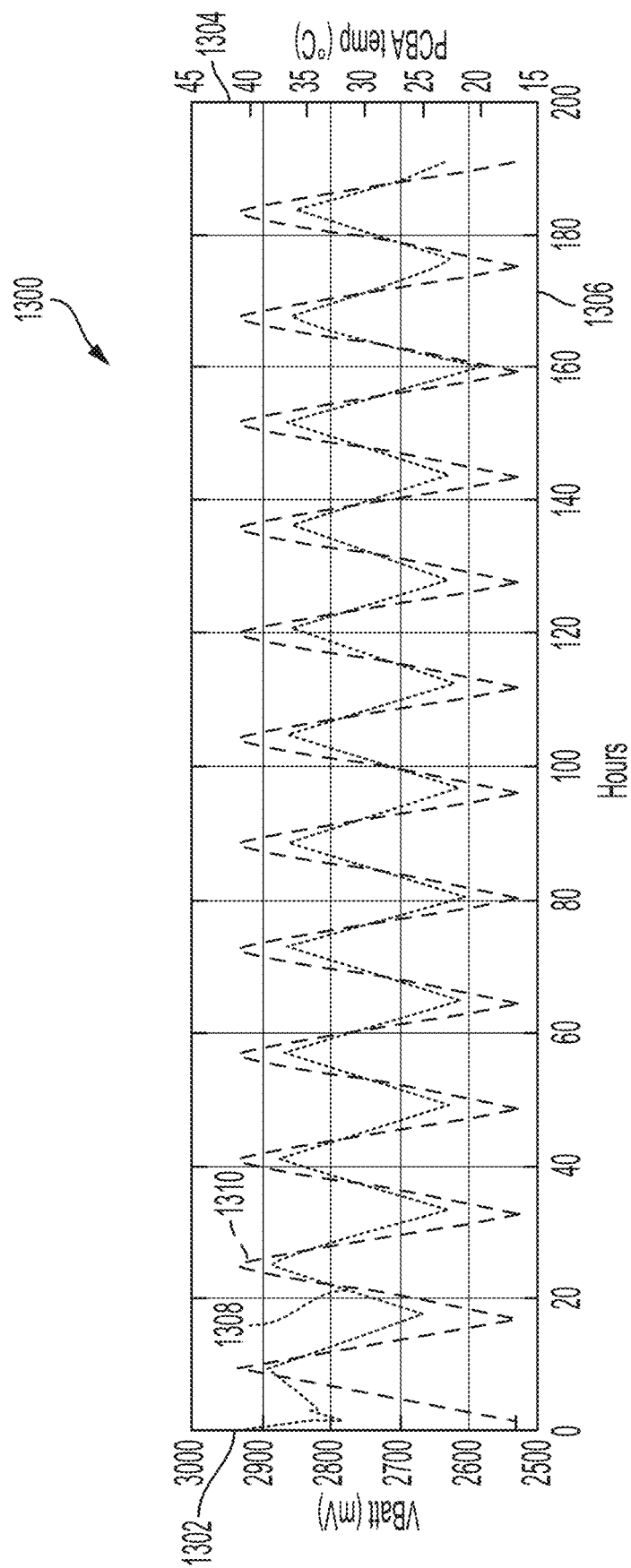
FIG. 13 illustrates a graph of battery voltage and printed circuit board assembly (PCBA) temperature over time, in accordance with at least one aspect of the present disclosure.

In the process 900 illustrated in FIG. 9A, the control circuit utilizes these received 902 battery voltage measurements for monitoring the state of the receiver 102. However, battery voltage can be temperature dependent; therefore, the temperature of the receiver 102 can impact the performance and life of the power source 114 of the receiver 102. For example, FIG. 13 depicts a graph 1300 illustrating experimental data of the relationship between battery voltage and temperature. The graph 1300 has a first vertical axis 1302 representing battery voltage of the receiver 102, a second vertical axis 1304 representing temperature of the receiver 102 (e.g., the temperature of the PCBA of the strip 106), and a horizontal axis 1306 representing time (e.g., in hours). A first line 1308 indicates the change in battery voltage (represented by the first vertical axis 1302) over time and a second line 1310 indicates change in PCBA temperature (represented by the second vertical axis 1304) over time. In this particular experiment, a set of batteries were placed in an oven that was programmed to cycle through temperatures of 15-40° C. in 5° C. steps and the battery voltages were measured throughout. As can be seen from the graph 1300, as the PCBA temperature is oscillated between 15° C. and 40° C. (represented by the second line 1310), the battery voltage of the receiver 102 (represented by the first line 1308) correspondingly oscillates in accordance with the changing PCBA temperature. Therefore, in another aspect, the control circuit can execute a process 901 that is configured to adjust or normalize the received 902 battery voltage measurements according to the detected temperate of the receiver 102 to account for the temperature effect on the performance of the battery. Accordingly, the control circuit executing the process 901 illustrated in FIG. 9B receives 903a temperature measurements of the receiver 102 from the temperature sensor 128. In one aspect, the temperature sensor 128 can be configured to measure the temperature of the PCBA supporting or disposed within the strip 106. In various aspects, the receiver temperature can be measured and/or received 903a by the control circuit prior to, simultaneously to, or after the battery voltage measurement is measured and/or received 902.

Figure 14:
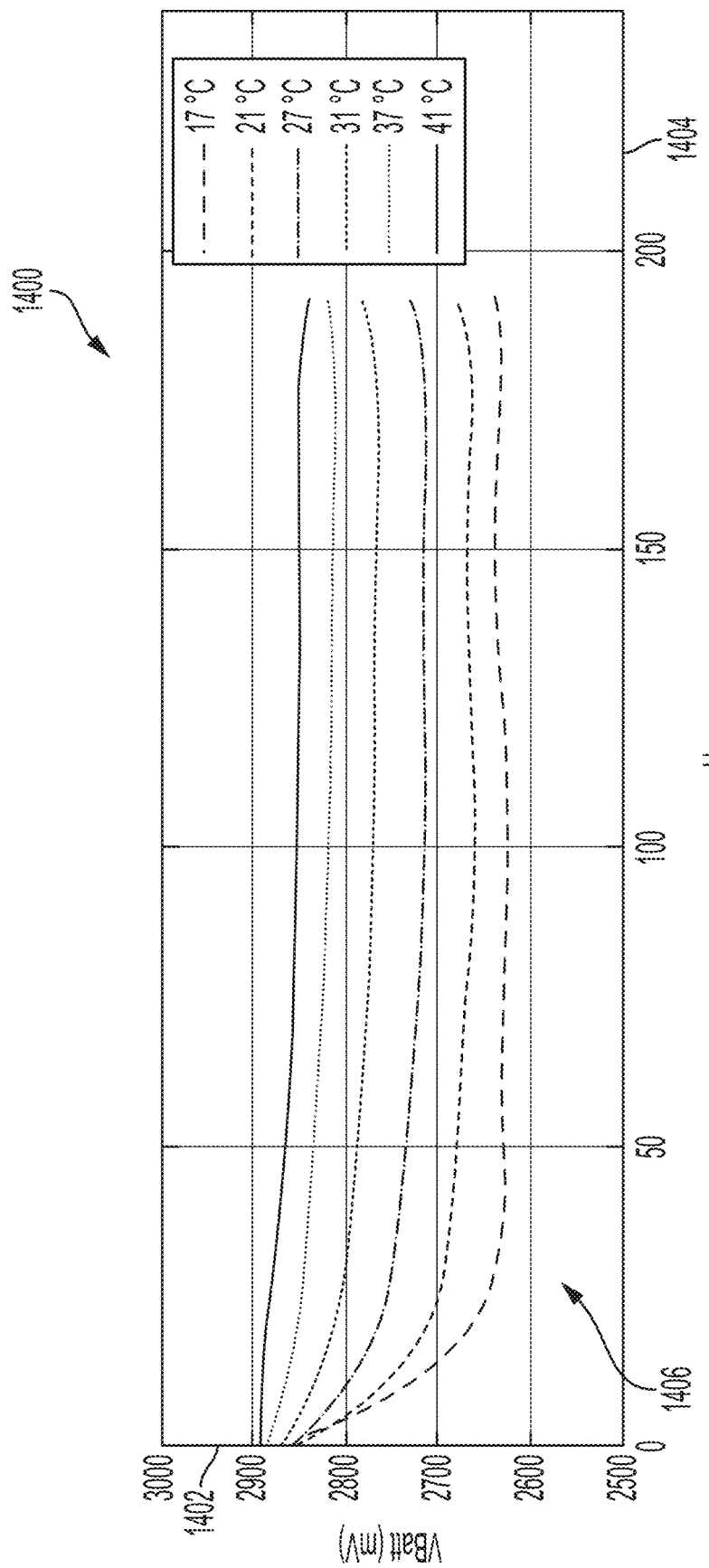
FIG. 14 illustrates a graph of interpolated battery voltage for various example temperatures, in accordance with at least one aspect of the present disclosure.
Figure 15:
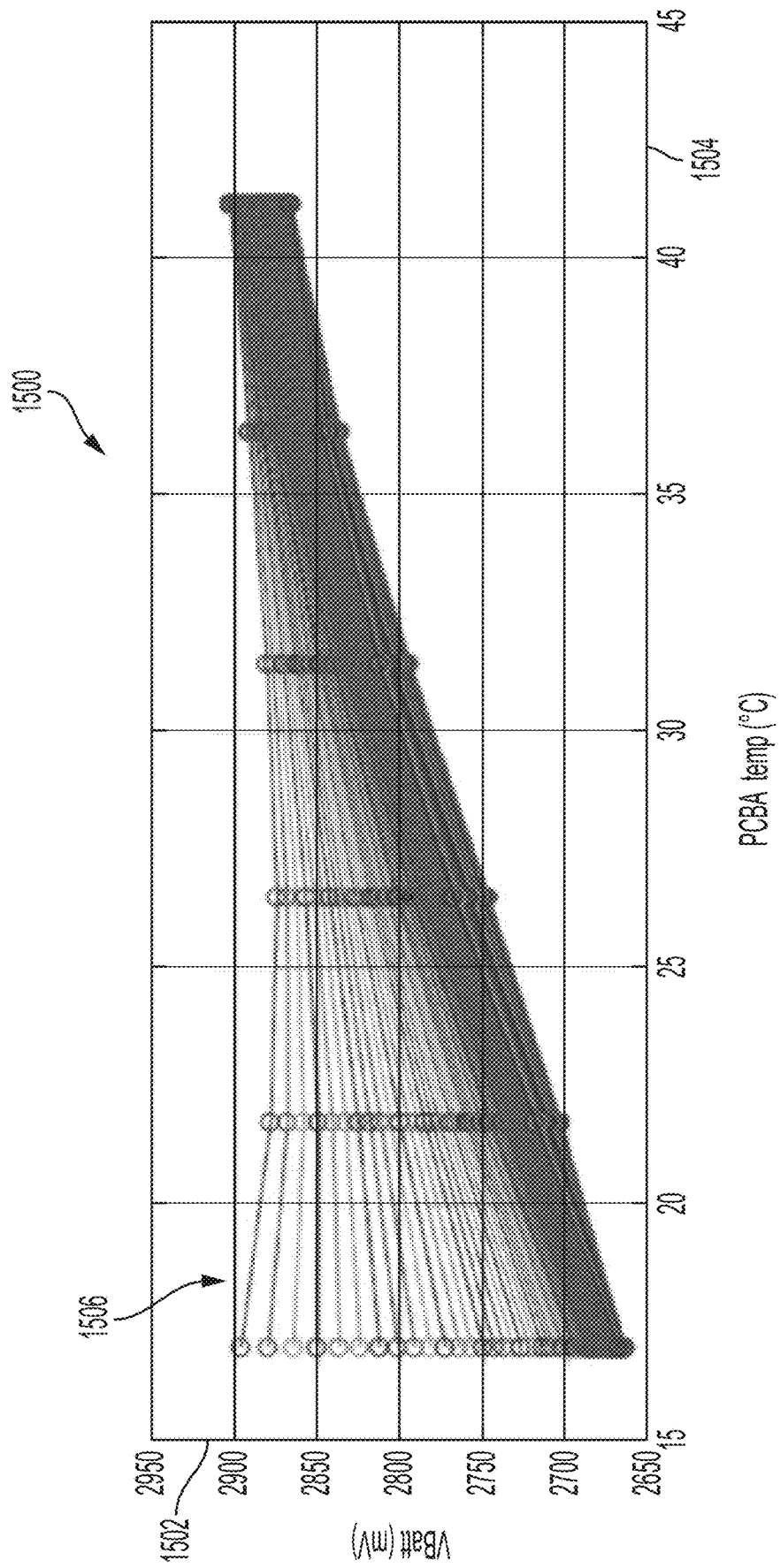
FIG. 15 illustrates a graph of a series of characterized battery voltage curves relative to PCBA temperature, in accordance with at least one aspect of the present disclosure.

Accordingly, the control circuit executing the process 901 determines 903b the normalized battery voltage based on the received 902 battery voltage and the received 903a temperature. In one aspect, the control circuit can determine 903b the normalized battery voltage by accessing pre-characterized data relating battery voltage data to PCBA temperature in the form of, for example, an algorithm or a lookup table. An algorithm and/or lookup table for use in normalizing battery voltage according to receiver temperature can be generated from experimentally determined temperature and battery voltage data utilizing a number of different techniques. For example, FIG. 14 illustrates a graph 1400 of interpolated battery voltage for various examples temperatures, where the vertical axis 1402 represents battery voltage and the horizontal axis 1404 represents time. In the graph 1400, the curves 1406 have been generated from the median battery voltage measurement data at each step of the experimental process represented by FIG. 13, binned into the appropriate temperature levels and then interpolated. Further, the interpolated battery voltage curves 1406 can be averaged across each of the tested batteries for each temperature level and then binned into, e.g., one hour increments. For each time increment, the battery voltage can be characterized as a function of temperature using a cubic regression to generate a family of curves relating battery voltage to temperature, as illustrated in FIG. 15. FIG. 15 illustrates a graph 1500 of a series of characterized battery voltage curves 1506 relative to PCBA temperature, where the vertical axis 1502 represents battery voltage and the horizontal axis 1504 represents PCBA temperature. Accordingly, the measured battery voltage can be normalized to a nominal temperature (e.g., 30° C.) based on which of the curves 1506 the measured battery voltage and measured temperature lies closest to. In another aspect, the curves 1506 can be averaged to produce a linear scaling factor. In this aspect, the control circuit can be configured to apply the linear scaling factor to received 902 battery voltage measurements to normalize the measured battery voltage. In practice, a linear scaling factor can result in higher battery voltage measurements being overadjusted; however, such overadjustments can be acceptable because it is more critical to properly calibrate lower battery voltage measurements because the lower measurements are what triggers the control circuit to provide an alert. The algorithms defining the curves 1506 and/or linear scaling factors can be stored (e.g., in the memory 160), translated into a lookup table (e.g., stored in the memory 160), or otherwise provided in a form for access by the control circuit executing the process 901 for determining 903b the normalized battery voltage.

In one aspect, the battery voltage and/or temperature of the receiver 102 can be measured at a fixed interval. In another aspect, the battery voltage and/or temperature can be measured at variable intervals. In this aspect, the interval at which the battery voltage and/or temperature is measured can be varied according to, for example, the state of the receiver 102 and/or in relation to other events. In one aspect, the battery voltage and/or temperature can be measured at a first interval (e.g., four minutes) during a time period (e.g., 20 minutes) after the control module 108 has been rebooted and a second interval (e.g., 20 minutes) thereafter. The control module 108 can be configured to reboot when, for example, first connected to or inserted in a strip 106.

The processes 900, 901 coincide with each other from this point forward and thus the remaining portions of the process 900, 901 will be discussed in conjunction with each other. Accordingly, the control circuit determines 904 the value of the battery voltage measurement (whether it is a raw battery voltage measurement, as in FIG. 9A, or a normalized battery voltage measurement, as in FIG. 9B) relative to a third or voltage threshold. In one aspect, the control circuit determines 904 whether the battery voltage measurement is greater than a voltage threshold. The voltage threshold can be set to an empirically determined level corresponding to a low battery level or a level at which the battery is expected to die shortly (e.g., 2,620 mV).

The processes 900, 901 executed by the control circuit can be programmed to track the number of consecutive "bad" voltage measurement readings. In one aspect, the control circuit is configured to track the number of voltage readings that fall below a predetermined threshold. For example, if the voltage measurement is above the threshold, then the processes 900, 901 proceed along the NO branch and the control circuit sets 906 the number of consecutive measurements to zero. The control circuit then continues receiving 902, 903a data measurements and otherwise proceeds as described above. If the voltage measurement is below the threshold, then the processes 900, 901 proceed along the YES branch and the control circuit increments 908 a counter tracking the number of consecutive measurements that exceeded the voltage threshold. Accordingly, the control circuit determines 910 whether the number of consecutive measurements exceeds a fourth threshold. If the number of consecutive measurements is not above the fourth threshold, then the processes 900, 901 proceed along the NO branch and the control circuit continues receiving 902, 903a data measurements and otherwise proceeds as described above. If the number of consecutive measurements is above the fourth threshold, then the processes 900, 901 proceed along the YES branch and the control circuit computes 912 an aggregate battery voltage.

Figure 10:
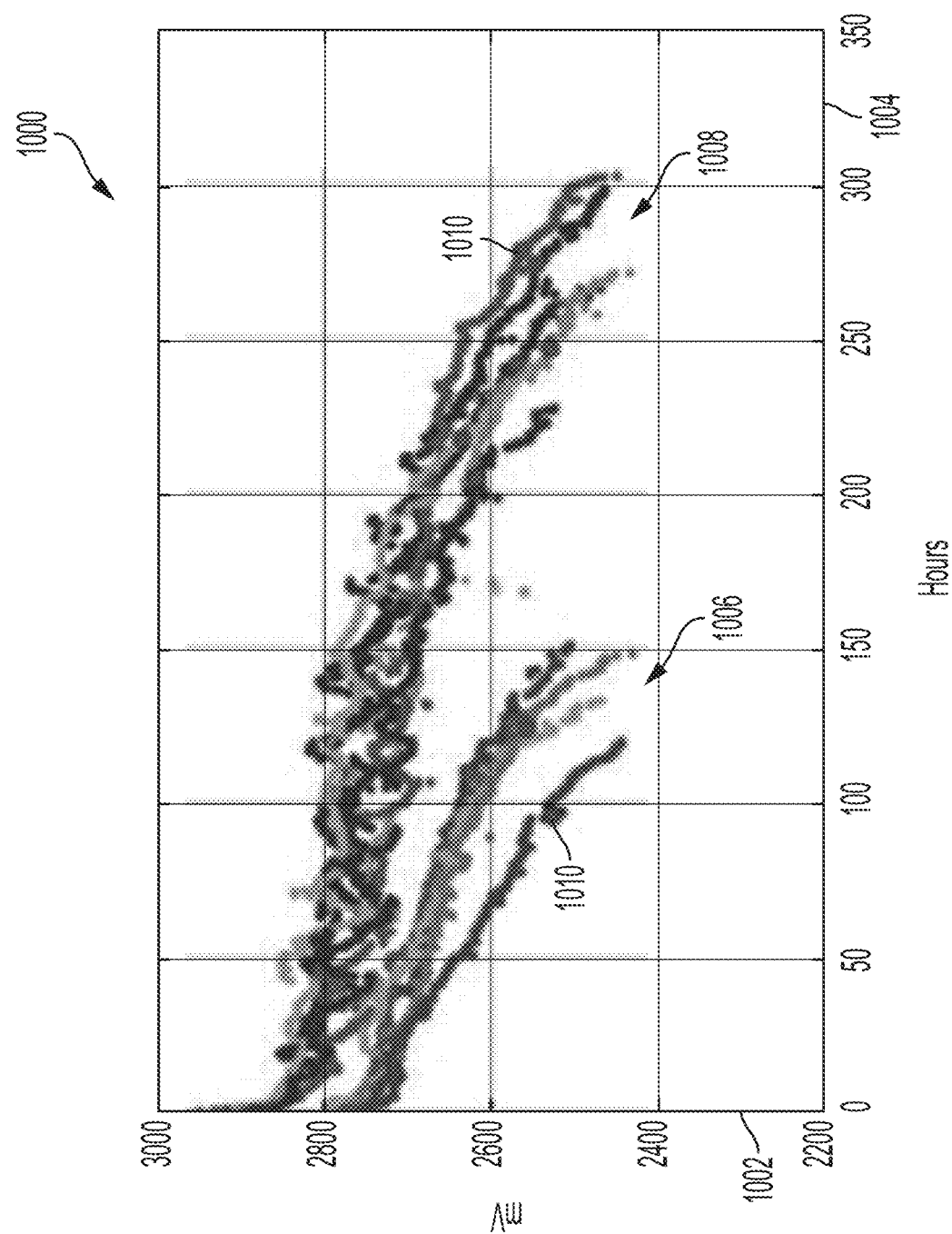
FIG. 10 illustrates a graph of battery voltage over time for various illustrative receiver assemblies, in accordance with at least one aspect of the present disclosure.

Accordingly, the control circuit computes 912 the aggregate battery voltage. The aggregate battery voltage can be calculated for a set time period or for a set number of battery voltage measurements. In one aspect, the aggregate battery voltage can be based on a running median of the battery voltage measurements. It can be desirable for the control circuit to compute 912 an aggregated battery voltage because individual battery voltage measurements tend to be noisy, especially when the receiver 102 is booting up and/or when the receiver 102 or components thereof are taking measurements. Therefore, after the requisite number of consecutive bad battery voltage measurements, the control circuit 10 implements an additional validation step to ensure that the battery voltage is in fact in the process of dying. In one aspect, the control circuit computes 912 the battery voltage over time by tracking the battery voltage for each time instance and then calculating the area under the curve defined by the tracked voltage and time values, as depicted in FIG. 10. FIG. illustrates a graph 1000, wherein the vertical axis 1002 represents battery voltage of the receiver 102, the horizontal axis 1004 represents time, and the points 1010 indicated for each curve represent the points at which one day of battery life remains. The area under the curve can be utilized for lithium-ion batteries, for example, because such batteries tend to have a flat discharge profile. Therefore, the battery voltage may drop below the voltage threshold well prior to the end of life of the battery but then stay at that voltage level for an extended period of time (e.g., a period of days). As a result, an alternative metric must be tracked to determine when in fact the power source 114 is actually approaching its end of life (e.g., when one day of battery life remains). The area under the curve between two points in time can be calculated via any appropriate method.

Accordingly, the control circuit determines 914 the value of the calculated voltage over time metric relative to one or more thresholds. In one aspect, the control circuit determines 914 whether the calculated aggregate voltage falls below an aggregate voltage threshold. If the aggregate voltage does not fall below the aggregate voltage threshold, then the processes 900, 901 proceed along the NO branch and the control circuit continues receiving 916 data measurements (e.g., battery voltage and/or receiver temperature), computing 912 the voltage-time metric, and then determining 914 whether the voltage-time metric falls below the voltage threshold. If the voltage-time metric does fall below the voltage threshold, then the processes 900, 901 proceed along the YES branch and the control circuit takes a corresponding action. In one aspect, the control circuit causes an alert to be provided 918 to the user.

Figure 11:
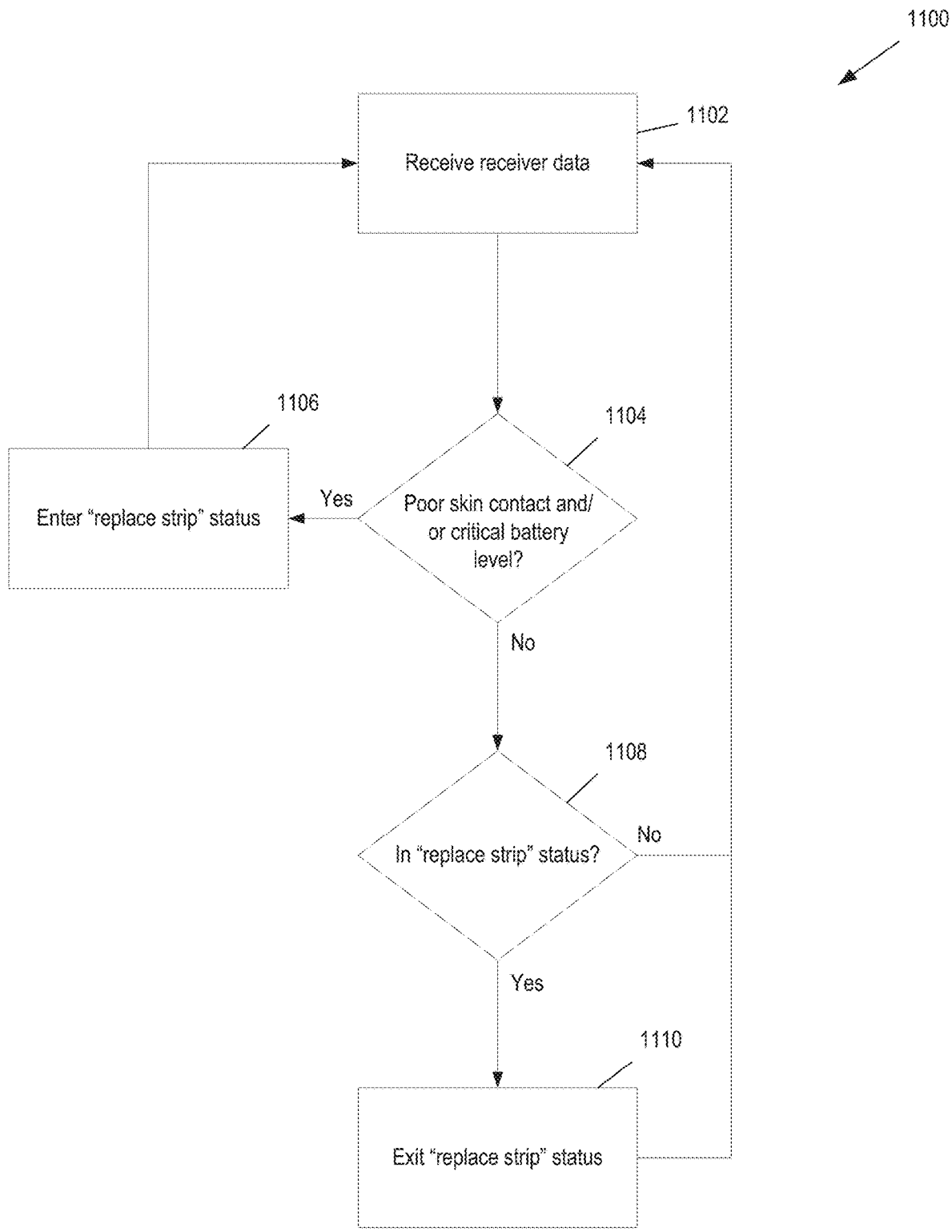
FIG. 11 illustrates a logic flow diagram of a first process for alerting a user to change a receiver, in accordance with at least one aspect of the present disclosure.

FIG. 11 illustrates a logic flow diagram of a first process 1100 for alerting a user to change a receiver 102, in accordance with at least one aspect of the present disclosure. In the following description of the process 1100, reference should also be made to FIGS. 1 and 6A-7. The processes 800, 900, 901 described above in connection with FIGS. 8, 9A, and 9B can be utilized in conjunction with each other to alert a user when it is necessary to replace the strip 106 of the receiver 102 due to poor skin contact and/or the power source 114 of the receiver 102 being at a critical power level. In one aspect, a control circuit executing the process 1100 for generating a strip change alert receives 1102 data from the receiver 102, such as impedance, temperature, and/or battery voltage measurements. The control circuit can receive this data from the impedance sensor 126, the temperature sensor 128, the voltage sensor 130, or as otherwise described above.

Accordingly, the control circuit determines 1104 whether there is poor skin contact between the receiver 102 and the wearer, such as via the process 800 described in connection with FIG. 8, and/or whether the power level of the receiver 102 is critical (i.e., whether the power source 114 is dying), such as via the processes 900, 901 described in connection with FIGS. 9A and 9B. If the skin contact is poor and/or the battery level is critical, then the process 1100 proceeds along the YES branch and the control circuit activates or causes the receiver 102 to enter 1106 the "replace strip" status. When the replace strip status is activated, the receiver 102 causes an alert to be provided to the user indicating that the strip 106 should be replaced. In various aspects, the receiver 102 can transmit a signal to a mobile device 150 that is connected (e.g., wirelessly) to the receiver 102, to back-end computer system 152 (e.g., a cloud computing system) that is connected (e.g., wirelessly) to the receiver 102 that then causes an alert (e.g., a push notification) to be transmitted to a mobile device 150 associated with the wearer of the receiver 102, and so on. If the skin contact is not poor and the battery level is not critical, then the process 1100 proceeds along the NO branch and the control circuit then determines 1108 whether the replace strip status is active. If the replace strip status is not active, then the process 1100 proceeds along the NO branch and the control circuit continues receiving 1102 data from the receiver 102. If the replace strip status is active, then the process 1100 proceeds along the YES branch and the control circuit exits 1110 or cancels the replace strip status and then continues receiving 1102 data from the receiver 102.

Figure 12:
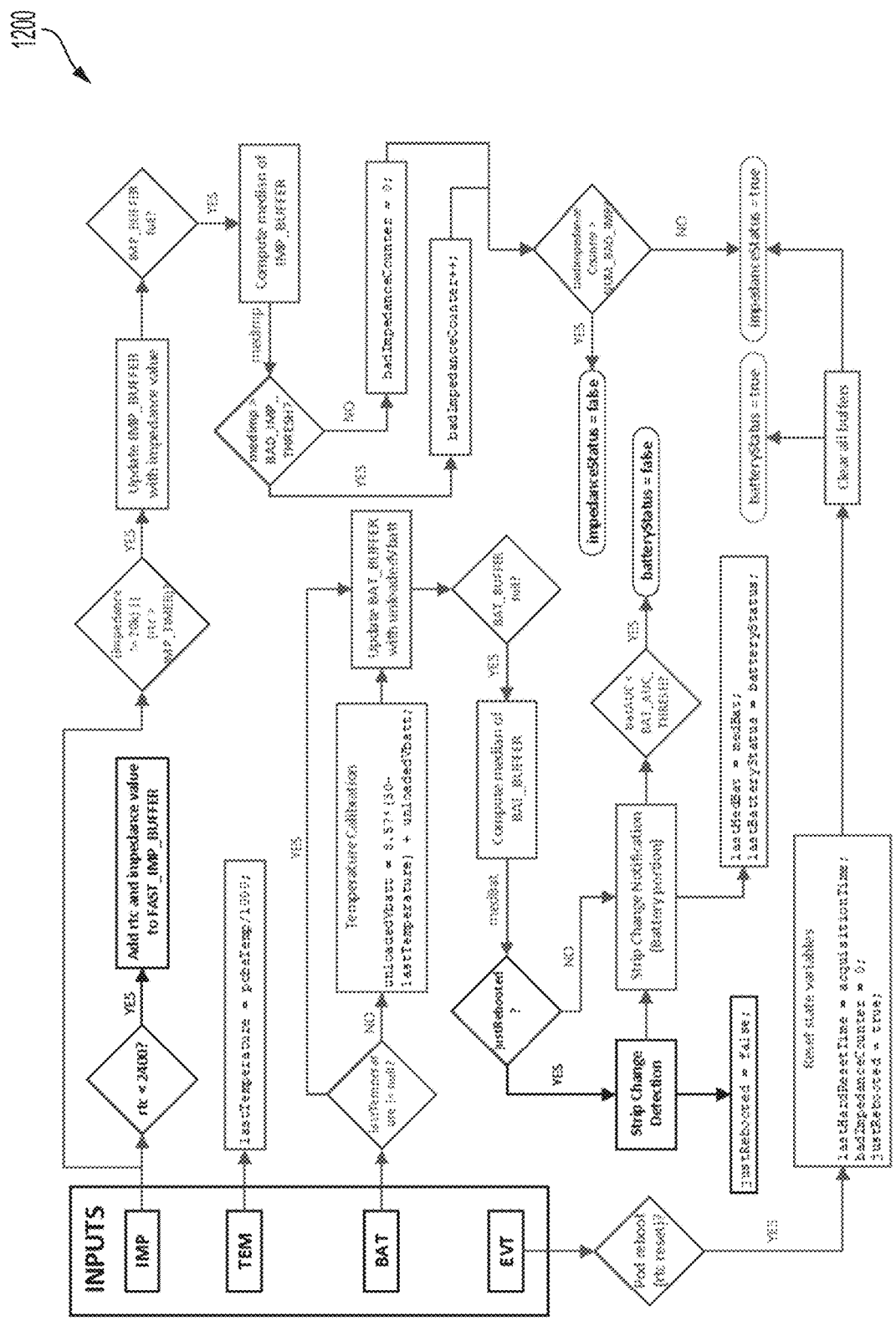
FIG. 12 illustrates a logic flow diagram of a second process for alerting a user to change a receiver, in accordance with at least one aspect of the present disclosure.

FIG. 12 illustrates a second process 1200 for alerting a user to change a receiver 102, in accordance with at least one aspect of the present disclosure. This process 1200 illustrates an alternative or expanded representation of the process 1100 illustrated in FIG. 11 including the processes 800, 901 in a single logic flow diagram. A control circuit executing this process 1200 likewise monitors impedance, battery voltage, and temperature data to determine whether to provide an alert to a user that the strip of the receiver assembly needs to be replaced (i.e., batteryStatus=false and/or impedanceStatus=false).

Strip Change Detection

Figure 16:
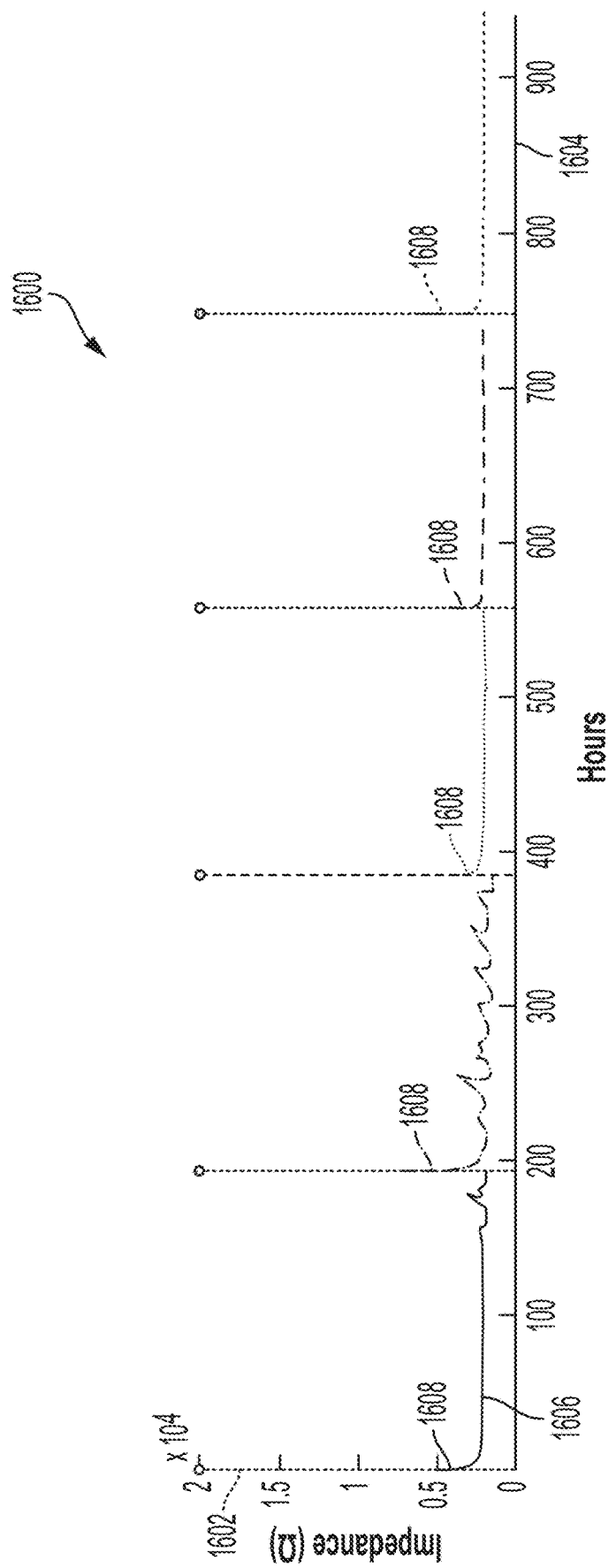
FIG. 16 illustrates a graph of impedance over time over the course of multiple adhesive strips being replaced in a receiver, in accordance with at least one aspect of the present disclosure.

In one aspect, the control module 108 pairs with a mobile device 150 when it is initially booted. In this aspect, subsequently replacing the adhesive strip 106 component of the receiver 102 does not generate a new pairing event between the control module 108 and the mobile device 150. Therefore, alternative data streams must be utilized in order to track when users are changing the adhesive strips 106 of the receiver 102. In various aspects of the receiver 102, the user replaces the adhesive strip 106 by disconnecting it from the control module 108. As the adhesive strip 106 contains the power source 114, this action therefore causes the control module 108 to deactivate. When the control module 108 is then connected to a fresh adhesive strip 106, the control module 108 reboots, creating a power cycle during which the control module 108 performs a power-on self-test (POST) process during which the impedance of the electrodes 112 can be monitored to determine whether the control module 108 has been coupled to a new adhesive strip 106 and then reapplied to the wearer's body. For example, FIG. 16 illustrates a graph 1600 of experimental data, where the vertical axis 1602 represents electrode impedance, the horizontal axis 1604 represents time, and each of the curves 1606 represent the electrode impedance experienced by the receiver 102 over the course of multiple replacement strips 106. As can be seen in FIG. 16, impedance sharply drops 1608 when a fresh adhesive strip 106 is connected to a control module 108. Therefore, this initial period of sharply declining impedance can be detected and characterized to determine when the adhesive strip 106 has been replaced. In one aspect, the control circuit is configured to sample impedance at a faster rate during an initial period after a reboot (e.g., during the POST process) in order to increase the resolution of the impedance measurement and thus assist in determining whether a fresh strip 106 has been connected to the control module 108. For example, the control circuit can sample the skin impedance at a first rate (e.g., every 30 seconds) during an interval (e.g., 20 minutes) after a reboot and then revert to a default or second impedance sampling rate (e.g., every 20 minutes) thereafter.

Determining when the adhesive strips 106 are replaced can be useful for a number of different reasons. For example, tracking replacement events for the strip 106 can be useful for business analytics purposes (e.g., tracking the number of adhesive strips 106 consumed and the compliance of users to the prescribed use of the receiver 102). As another example, tracking replacement events for the strip 106 can improve the breadth and usefulness of data made available to users via a mobile application (e.g., executed by a mobile device 150 paired with the receiver 102), such as by tracking and displaying for the user the number of days since the last instance that the adhesive strip was replaced. As yet another example, tracking replacement events for the strip 106 can improve the user experience, such as by allowing a mobile application to prompt the user to change the adhesive strip 106 and then confirm that the strip 106 has been changed thereafter. Prompting users to change the strip 106 regularly can be desirable because contact quality between the strip 106 and the wearer tends to degrade over time, reducing data quality and risking a failure event where the strip 106 becomes detached from the wearer, which could, in turn, cause the receiver 102 to miss signals from an ingested IEM and/or fail to receive other data.

Figure 17:
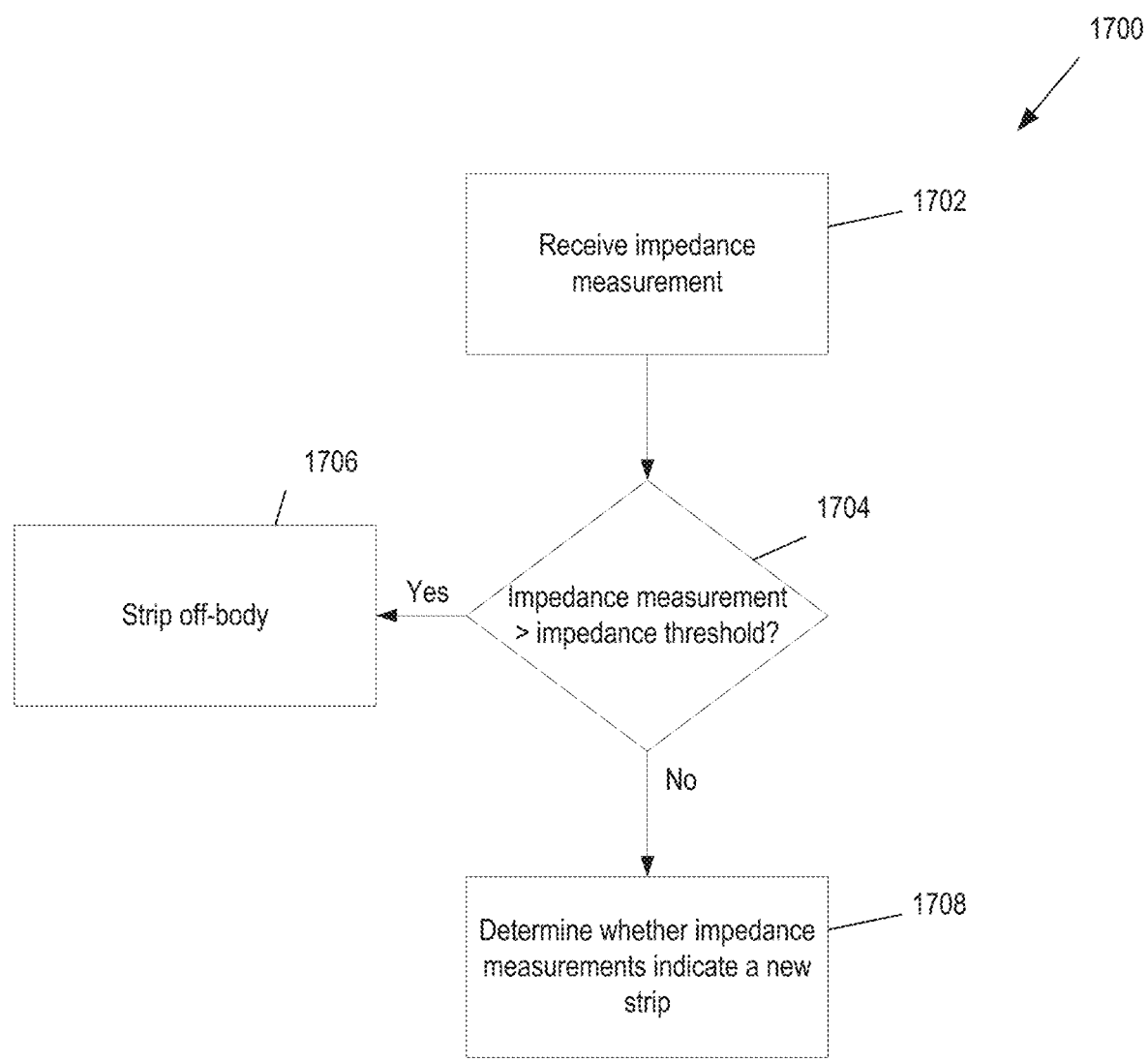
FIG. 17 illustrates a logic flow diagram of a process for monitoring impedance to detect a replacement adhesive strip, in accordance with at least one aspect of the present disclosure.

FIG. 17 illustrates a logic flow diagram of a process 1700 for monitoring impedance to detect a replacement adhesive strip 106, in accordance with at least one aspect of the present disclosure. The control circuit initially receives 1702 impedance measurement data from, e.g., the impedance sensor 126 of the receiver 102. In one aspect, the control circuit applies a median filter, running average, or another smoothing algorithm to the received 1702 impedance measurements to remove or mitigate false positives from noise.

Accordingly, the control circuit compares the impedance measurement(s) to an impedance threshold. In one aspect, the control circuit determines 1704 whether received impedance measurements are below an impedance threshold (e.g., 20,000 ohms) indicative of whether the receiver 102 is attached to a user's body. If the impedance measurements are above the threshold, then the process 1700 proceeds along the YES branch and the control circuit can determine 1706 that the strip is off-body. If the impedance measurement are below the threshold, then the process 1700 can continue.

Accordingly, the control circuit determines 1708 whether the impedance measurement data indicates that the control module 108 has been attached to a new, replacement adhesive strip 106. In one aspect, the control circuit determines the slope (M) or rate of change of the received impedance measurements. If the user has connected the control module 108 to a new adhesive strip 106, M should be a large negative number since impedance will start out high and drop down quickly (as shown in FIG. 16). If the user has reconnected the control module 108 to the same strip 106 or another strip 106 that has been previously used, M should be close to zero since impedance should already be stable for that strip 106. Further, the control circuit determines the amount or degree of noisiness of the received impedance measurements. In one aspect, the control circuit calculates the Pearson's coefficient (R) of the received impedance measurements, which indicates how noisy the impedance measurements are. If R is close to zero, it means the measurements are very noisy and hence unreliable. Thus, the control circuit can utilize R to prevent false detections from occurring when impedance is noisy. Accordingly, the control circuit can compare the calculated values of M and/or R to corresponding thresholds and thereby determine whether the control module 108 has been connected to a new, replacement adhesive strip 106. In one aspect, the control circuit can determine whether M<a first threshold. In another aspect, the control circuit can determine whether M<a second threshold and R is <a third threshold. For example, the control circuit can determine that the control module 108 has been connected to a replacement strip 106 when M<−2 or (M<−0.1 and R<−0.7).

In another aspect, the control circuit can determine 1708 whether the impedance measurement data indicates that the control module 108 has been attached to a new, replacement adhesive strip 106 by characterizing the profile of the received impedance measurements. In this aspect, the control circuit can be configured to analyze all of the impedance measurements collected during the fast rate interval following a reboot of the control module (e.g., in a 2D array). As the expected impedance decay during the interval following a reboot is expected to follow a linear decay profile, an exponential decay profile, or a decay profile somewhere therebetween, the control circuit can calculate linear and/or exponential regressions (and the $R^2$ value therefor) for the collected impedance measurements and compare the calculated values to corresponding thresholds. If there is a strong linear or exponential fit and a relatively large negative slope, the control circuit can thereby determine that the control module 108 has been connected to a new adhesive strip 106.

In various other aspects, the control circuit can determine 1708 whether the impedance measurement data indicates that the control module 108 has been attached to a new, replacement adhesive strip 106 utilizing various statistical classification and/or machine-learning models. For example, the control circuit can execute a binary classifier trained to distinguish between impedance data from a new adhesive strip 106 being attached to the control module 108 and the old strip 106 being reattached to the control module 108 according to the calculated regressions and/or slope. As another example, the control circuit can be configured to execute a support vector machine (SVM) trained on labeled data (e.g., impedance data labeled with "new strip" and "old strip") in the multidimensional feature space to maximize the separation between the two categories (i.e., "new strip" and "old strip") by minimizing the objective function:

$$\frac{1}{2}\vec{\omega}^T\vec{\omega} + C\sum_{i=1}^{m}\varepsilon_i$$

such that $$y_i(\vec{x}_i^T\vec{\omega}+b) \geq 1-\varepsilon_i$$

where ($\vec{x}_i^T$, $y_i$) represents the set of features and their labels ($y_i=1$ for new strip, $y_i=-1$ for old strip), m is the number of observations (i.e., reboot events), C is the cost parameter that defines the penalty for a misclassification, and $\varepsilon_i$ represents the number of misclassifications. In addition to $\varepsilon_i$, the SVM model seeks to optimize $\vec{\omega}$, and b, which describe the multidimensional hyperplane satisfying $$\vec{\omega} \cdot \vec{x}_i^T - b = 0.$$

In another aspect, the control circuit can be configured to utilize battery voltage and may be used as a secondary metric to detect when the replacement of the adhesive strip 106 takes place, such as in situations where impedance is noisy or does not follow the typical decay profile after an adhesive strip 106 is replaced. For example, the control circuit can be configured to determine the ESR as the difference between the unloaded and loaded battery voltage (VBatt). As ESR increases over time for a battery and is a robust indicator of battery life, a significant (e.g., 30%) drop in ESR is a likely indicator of strip change. However, ESR alone may not be a robust indicator of strip change because users may change their strip even if the battery is still fresh. Accordingly, in one aspect, the control circuit can compute the rate of change of the ESR, compare the rate of the change of the ESR to a corresponding threshold, and thereby determine whether the control module has been connected to a replacement adhesive strip. The process of utilizing ESR to detect whether an adhesive strip has been replaced can be utilized in addition to or in lieu of the process 1700 of utilizing impedance to detect the same.

In yet another aspect, instead of or in addition to measuring the skin impedance, as discussed above with respect to FIG. 17, the receiver 102 can be configured to measure the user's ECG to determine whether the receiver 102 is attached to a user. In this aspect, ECG data can be sampled through the electrodes 112 at a fixed or variable time interval (e.g., every five minutes). The collected ECG data can then be input by a control circuit to a statistical classification system or machine-learning system, such as a neural network classifier that has been trained on a training data set to detect ECG signals. Thus, the control circuit can determine whether an ECG signal is detectable and accordingly determine whether the receiver 102 is currently being worn by a user (i.e., whether the electrodes are in contact with the user's skin and receiving a suitable signal thereby).

EXAMPLES

Various aspects of the subject matter described herein are set out in the following numbered examples:

Example 1

A computer-implemented method of monitoring a receiver, wherein the receiver comprises a strip and a control module removably connectable to the strip, the strip comprising an adhesive surface for attachment to a body of a user, the strip comprising an electrode configured to be situated against the body of the user, the control module comprising an impedance sensor configured to detect an impedance of the electrode when the control module is connected to the strip, the method comprising: receiving, by a device that is communicably couplable to the control module of the receiver, a skin impedance measurement of the electrode of the strip from the impedance sensor of the control module; determining, by the device, whether the skin impedance measurement exceeds an impedance threshold; counting, by the device, a consecutive number of skin impedance measurements that exceed the impedance threshold; and providing, by the device, an alert according to whether the consecutive number of skin impedance measurements exceeds a threshold.

Example 2

The computer-implemented method of Example 1, wherein the impedance threshold comprises 20,000 ohms.

Example 3

The computer-implemented method of Example 1, wherein the impedance threshold comprises 10,000 ohms.

Example 4

The computer-implemented method of any one of Examples 1-3, wherein providing the alert comprises displaying, by the device, a push notification.

Example 5

The computer-implemented method of any one of Examples 1-4, wherein the device is communicably connectable to the receiver via a Bluetooth Low Energy connection.

Example 6

The computer-implemented method of Examples 1-5, wherein the receiver is configured to receive a signal from an ingestible event marker conductively transmitted through the body of the user after ingestion of the ingestible event marker.

Example 7

The computer-implemented method of any one of Examples 1-6, wherein the method comprises: receiving, by the device, a plurality of skin impedance measurements at a first rate during a time period; and receiving, by the device, the plurality of skin impedance measurements at a second rate after the time period.

Example 8

The computer-implemented method of Example 7, wherein the time period begins when the control module is connected to the strip.

Example 9

The computer-implemented method of Example 7 or 8, wherein the first rate is greater than the second rate.

Example 10

A device communicably connectable to a receiver, wherein the receiver comprises a strip and a control module removably connectable to the strip, the strip comprising an adhesive surface for attachment to a body of a user, the strip comprising an electrode configured to be situated against the body of the user, the control module comprising an impedance sensor configured to detect an impedance of the electrode when the control module is connected to the strip, the device comprising: a processor; and a memory coupled to the processor, the memory storing instructions that, when executed by the processor, cause the device to: receive a skin impedance measurement of the electrode of the strip from the impedance sensor of the control module; determine whether the skin impedance measurement exceeds an impedance threshold; count a consecutive number of skin impedance measurements that exceed the impedance threshold; and provide an alert according to whether the consecutive number of skin impedance measurements exceeds a threshold.

Example 11

The device of Example 10, wherein the impedance threshold comprises 20,000 ohms.

Example 12

The device of Example 10, wherein the impedance threshold comprises 10,000 ohms.

Example 13

The device of any one of Examples 10-12, wherein the instructions, when executed by the processor, cause the device to provide the alert by causing the device to display a push notification.

Example 14

The device of any one of Examples 10-13, wherein the device is communicably connectable to the receiver via a Bluetooth Low Energy connection.

Example 15

The device of any one of Examples 10-14, wherein the receiver is configured to receive a signal from an ingestible event marker conductively transmitted through the body of the user after ingestion of the ingestible event marker.

Example 16

The device of any one of Examples 10-15, wherein the instructions, when executed by the processor, further cause the device to: receive a plurality of skin impedance measurements at a first rate during a time period; and receive the plurality of skin impedance measurements at a second rate after the time period.

Example 17

The device of Example 16, wherein the time period begins when the control module is connected to the strip.

Example 18

The device of Example 16 or 17, wherein the first rate is greater than the second rate.

Example 19

The device of any one of Examples 10-18, wherein the device comprises a smartphone.

Example 20

A computer-implemented method of monitoring a receiver, wherein the receiver comprises a strip and a control module removably connectable to the strip, the strip comprising an adhesive surface for attachment to a body of a user, the strip comprising an electrode configured to be situated against the body of the user, the strip comprising a power source, the control module comprising a voltage sensor configured to detect a voltage of the power source when the control module is connected to the strip, the control module comprising a temperature sensor configured to detect a temperature of the strip when the control module is connected to the strip, the method comprising: receiving, by a device that is communicably couplable to the control module of the receiver, a voltage measurement of the power source from the voltage sensor of the control module; receiving, by the device, a temperature measurement of the strip from the temperature sensor of the control module; normalizing, by the device, the voltage measurement according to the temperature measurement to generate a normalized voltage measurement; determining, by the device, whether the normalized voltage measurement falls below a voltage threshold; counting, by the device, a consecutive number of normalized voltage measurements that fall below the voltage threshold; calculating, by the device, an aggregate voltage according to whether the consecutive number of normalized voltage measurements exceeds a threshold; determining, by the device, whether the calculated aggregate voltage falls below an aggregate voltage threshold; and providing, by the device, an alert according to whether the calculated aggregate voltage falls below the aggregate voltage threshold.

Example 21

The computer-implemented method of Example 20, wherein normalizing the voltage measurement according to the temperature measurement comprises: applying, by the device, a scaling factor corresponding to the temperature measurement to the voltage measurement.

Example 22

The computer-implemented method of Example 20, wherein normalizing the voltage measurement according to the temperature measurement comprises: normalizing, by the device, the voltage measurement to a nominal temperature associated with one of a plurality of characterized battery voltage curves to which the voltage measurement and the temperature measurement corresponds.

Example 23

The computer-implemented method of any one of Examples 20-22, wherein computing the aggregate voltage comprises: plotting, by the device, a curve of the voltage measurement over time; and computing, by the device, an area under the curve for a time interval.

Example 24

The computer-implemented method of any one of Examples 20-23, wherein providing the alert comprises displaying, by the device, a push notification.

Example 25

The computer-implemented method of any one of Examples 20-24, wherein the device is communicably connectable to the receiver via a Bluetooth Low Energy connection.

Example 26

The computer-implemented method of any one of Examples 20-25, wherein the receiver is configured to receive a signal from an ingestible event marker conductively transmitted through the body of the user after ingestion of the ingestible event marker.

Example 27

The computer-implemented method of any one of Examples 20-26, wherein the method comprises: receiving, by the device, a plurality of voltage measurements at a first rate during a time period; and receiving, by the device, the plurality of voltage measurements at a second rate after the time period.

Example 28

The computer-implemented method of Example 27, wherein the time period begins when the control module is connected to the strip.

Example 29

The computer-implemented method of Example 27 or 28, wherein the first rate is greater than the second rate.

Example 30

A device communicably connectable to a receiver, wherein the receiver comprises a strip and a control module removably connectable to the strip, the strip comprising an adhesive surface for attachment to a body of a user, the strip comprising an electrode configured to be situated against the body of the user, the strip comprising a power source, the control module comprising a voltage sensor configured to detect a voltage of the power source when the control module is connected to the strip, the control module comprising a temperature sensor configured to detect a temperature of the strip when the control module is connected to the strip, the device comprising: a processor; and a memory coupled to the processor, the memory storing instructions that, when executed by the processor, cause the device to: receive a voltage measurement of the power source from the voltage sensor of the control module; receive a temperature measurement of the strip from the temperature sensor of the control module; normalize the voltage measurement according to the temperature measurement to generate a normalized voltage measurement; determine whether the normalized voltage measurement falls below a voltage threshold; count a consecutive number of normalized voltage measurements that fall below the voltage threshold; calculate an aggregate voltage according to whether the consecutive number of normalized voltage measurements exceeds a threshold; determine whether the calculated aggregate voltage falls below an aggregate voltage threshold; and provide an alert according to whether the calculated aggregate voltage falls below the aggregate voltage threshold.

Example 31

The device of Example 30, wherein the instructions, when executed by the processor, cause the device to normalize the voltage measurement by causing the device to: apply a scaling factor corresponding to the temperature measurement to the voltage measurement.

Example 32

The device of Example 30, wherein the instructions, when executed by the processor, cause the device to normalize the voltage measurement by causing the device to: normalize the voltage measurement to a nominal temperature associated with one of a plurality of characterized battery voltage curves to which the voltage measurement and the temperature measurement corresponds.

Example 33

The device of any one of Examples 30-32, wherein the instructions, when executed by the processor, cause the device to compute the aggregate voltage by causing the device to: plot a curve of the voltage measurement over time; and compute an area under the curve for a time interval.

Example 34

The device of any one of Examples 30-33, wherein providing the alert comprises displaying, by the device, a push notification.

Example 35

The device of any one of Examples 30-34, wherein the device is communicably connectable to the receiver via a Bluetooth Low Energy connection.

Example 36

The device of any one of Examples 30-35, wherein the receiver is configured to receive a signal from an ingestible event marker conductively transmitted through the body of the user after ingestion of the ingestible event marker.

Example 37

The device of any one of Examples 30-36, wherein the instructions, when executed by the processor, further cause the device to: receive a plurality of voltage measurements at a first rate during a time period; and receive the plurality of voltage measurements at a second rate after the time period.

Example 38

The device of Example 37, wherein the time period begins when the control module is connected to the strip.

Example 39

The device of Example 37 or 38, wherein the first rate is greater than the second rate.

Example 40

The device of any one of Examples 30-39, wherein the device comprises a smartphone.

Example 41

A computer-implemented method of monitoring a receiver, wherein the receiver comprises a strip and a control module removably connectable to the strip, the strip comprising an adhesive surface for attachment to a body of a user, the strip comprising an electrode configured to be situated against the body of the user, the strip comprising a power source, the control module comprising a voltage sensor configured to detect a voltage of the power source when the control module is connected to the strip, the control module comprising a temperature sensor configured to detect a temperature of the strip when the control module is connected to the strip, the control module comprising an impedance sensor configured to detect an impedance of the electrode when the control module is connected to the strip, the method comprising: receiving, by a device that is communicably couplable to the control module of the receiver, a skin impedance measurement of the electrode of the strip from the impedance sensor of the control module; receiving, by the device, a voltage measurement of the power source from the voltage sensor of the control module; receiving, by the device, a temperature measurement of the strip from the temperature sensor of the control module; determining, by the device, whether the skin impedance measurement exceeds an impedance threshold; counting, by the device, a consecutive number of skin impedance measurements that exceed the impedance threshold; normalizing, by the device, the voltage measurement according to the temperature measurement to generate a normalized voltage measurement; determining, by the device, whether the normalized voltage measurement falls below a voltage threshold; counting, by the device, a consecutive number of normalized voltage measurements that fall below the voltage threshold; calculating, by the device, an aggregate voltage according to whether the consecutive number of normalized voltage measurements exceeds a first count threshold; determining, by the device, whether the calculated aggregate voltage falls below an aggregate voltage threshold; and providing, by the device, an alert according to whether at least one of the consecutive number of skin impedance measurements exceeds a second count threshold or the calculated aggregate voltage falls below the aggregate voltage threshold.

Example 42

The computer-implemented method of Example 41, wherein the impedance threshold comprises 20,000 ohms.

Example 43

The computer-implemented method of Example 41, wherein the impedance threshold comprises 10,000 ohms.

Example 44

The computer-implemented method of any one of Examples 41-43, wherein normalizing the voltage measurement according to the temperature measurement comprises: applying, by the device, a scaling factor corresponding to the temperature measurement to the voltage measurement.

Example 45

The computer-implemented method of any one of Examples 41-43, wherein normalizing the voltage measurement according to the temperature measurement comprises: normalizing, by the device, the voltage measurement to a nominal temperature associated with one of a plurality of characterized battery voltage curves to which the voltage measurement and the temperature measurement corresponds.

Example 46

The computer-implemented method of any one of Examples 41-45, wherein computing the aggregate voltage comprises: plotting, by the device, a curve of the voltage measurement over time; and computing, by the device, an area under the curve for a time interval.

Example 47

The computer-implemented method of any one of Examples 41-46, wherein providing the alert comprises displaying, by the device, a push notification.

Example 48

The computer-implemented method of any one of Examples 41-47, wherein the device is communicably connectable to the receiver via a Bluetooth Low Energy connection.

Example 49

The computer-implemented method of any one of Examples 41-48, wherein the receiver is configured to receive a signal from an ingestible event marker conductively transmitted through the body of the user after ingestion of the ingestible event marker.

Example 50

The computer-implemented method of any one of Examples 41-49, wherein the method comprises: receiving, by the device, a plurality of voltage measurements at a first rate during a time period and plurality of skin impedance measurements at a second rate; and receiving, by the device, the plurality of voltage measurements at a third rate and the plurality of skin impedance measurements at a fourth rate after the time period.

Example 51

The computer-implemented method of Example 50, wherein the time period begins when the control module is connected to the strip.

Example 52

The computer-implemented method of Example 50 or 51, wherein the first rate is greater than the third rate and the second rate is greater than the fourth rate.

Further, U.S. Provisional Patent Application No. 62/685,878, titled LOW POWER RECEIVER FOR IN VIVO CHANNEL SENSING AND INGESTIBLE SENSOR DETECTION WITH WANDERING FREQUENCY, filed Jun. 15, 2018; International Application No. PCT/US2019/037307, titled LOW POWER RECEIVER FOR IN VIVO CHANNEL SENSING AND INGESTIBLE SENSOR DETECTION WITH WANDERING FREQUENCY, filed Jun. 14, 2019; U.S. Provisional Patent Application No. 62/685,784, titled RE-WEARABLE PHYSIOLOGICAL MONITORING DEVICE, filed Jun. 15, 2018; and International Application No. PCT/US2019/037382, titled RE-WEARABLE PHYSIOLOGICAL MONITORING DEVICE, filed Jun. 14, 2019 are each hereby incorporated herein by reference in their entireties.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those skilled in the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one skilled in the art in light of this disclosure. In addition, those skilled in the art will appreciate that the mechanisms of the subject matter described herein are capable of being distributed as one or more program products in a variety of forms, and an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer-readable media. Thus a machine-readable medium may include any mechanism for storing or transmitting information in a form readable by a machine (e.g., a computer), including, but not limited to, floppy diskette, optical disk, compact disc read-only memory (CD-ROM), magneto-optical disk, read-only memory (ROM), random access memory (RAM), erasable programmable read-only memory (EPROM), electrically erasable programmable read-only memory (EEPROM), magnetic or optical card, flash memory, or a tangible, machine-readable storage used in the transmission of information over the Internet via electrical, optical, acoustical, or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or FPGA), state machine circuitry, firmware that stores instructions executed by programmable circuitry, and any combination thereof. The control circuit may, collectively or individually, be embodied as circuitry that forms part of a larger system, for example, an IC, an ASIC, a SoC, desktop computers, laptop computers, tablet computers, servers, smart phones, etc. Accordingly, as used herein, "control circuit" includes, but is not limited to, electrical circuitry having at least one discrete electrical circuit, electrical circuitry having at least one IC, electrical circuitry having at least one application-specific IC, electrical circuitry forming a general-purpose computing device configured by a computer program (e.g., a general-purpose computer configured by a computer program that at least partially carries out processes and/or devices described herein or a microprocessor configured by a computer program that at least partially carries out processes and/or devices described herein), electrical circuitry forming a memory device (e.g., forms of RAM), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware, and/or circuitry configured to perform any of the aforementioned operations. Software may be embodied as a software package, code, instructions, instruction sets, and/or data recorded on non-transitory computer-readable storage medium. Firmware may be embodied as code, instructions or instruction sets, and/or data that are hard-coded (e.g., nonvolatile) in memory devices.

As used in any aspect herein, the terms "component," "system," "module," and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states that may, though they need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol, which may be capable permitting communication using a Transmission Control Protocol/Internet Protocol (TCP/IP). The Ethernet protocol may comply or be compatible with the Ethernet standard published by the Institute of Electrical and Electronics Engineers (IEEE), titled "IEEE 802.3 Standard," published in December 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001 and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components, inactive-state components, and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to"). It will be further understood by those skilled in the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include, but not be limited to, systems that have A alone, B alone, C alone, A and B together, A and C together, B and C together, and/or A, B, and C together). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A," "B," or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures, or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

In summary, numerous benefits have been described that result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A computer-implemented method of monitoring a receiver, wherein the receiver comprises a disposable strip and a reusable control module removably connectable to the disposable strip, the disposable strip comprising an adhesive surface for attachment to a body of a user, the disposable strip comprising an electrode configured to be situated against the body of the user, the disposable strip comprising a power source, the reusable control module lacking its own power source and comprising a voltage sensor and a temperature sensor, the method comprising:
   powering on the reusable control module when the reusable control module is connected to the disposable strip;
   detecting, by the voltage sensor, a voltage measurement of the power source when the reusable control module is connected to the disposable power strip;
   detecting, by the temperature sensor, a temperature measurement of the disposables strip when the reusable control module is connected to the disposable strip;
   receiving, by a device that is communicably couplable to the reusable control module of the receiver, the voltage measurement of the power source from the voltage sensor of the reusable control module;
   receiving, by the device, the temperature measurement of the disposable strip from the temperature sensor of the reusable control module;
   normalizing, by the device, the voltage measurement according to the temperature measurement to generate a normalized voltage measurement;
   determining, by the device, whether the normalized voltage measurement falls below a voltage threshold;
   counting, by the device, a consecutive number of normalized voltage measurements that fall below the voltage threshold;
   calculating, by the device, an aggregate voltage according to whether the consecutive number of normalized voltage measurements exceeds a threshold;
   determining, by the device, whether the calculated aggregate voltage falls below an aggregate voltage threshold; and
   providing, by the device, an alert according to whether the calculated aggregate voltage falls below the aggregate voltage threshold.

2. The computer-implemented method of claim 1, wherein normalizing the voltage measurement according to the temperature measurement comprises:
   applying, by the device, a scaling factor corresponding to the temperature measurement to the voltage measurement.

3. The computer-implemented method of claim 1, wherein normalizing the voltage measurement according to the temperature measurement comprises:
   normalizing, by the device, the voltage measurement to a nominal temperature associated with one of a plurality of characterized battery voltage curves to which the voltage measurement and the temperature measurement corresponds.

4. The computer-implemented method of claim 1, wherein computing the aggregate voltage comprises:
   plotting, by the device, a curve of the voltage measurement over time; and
   computing, by the device, an area under the curve for a time interval.

5. The computer-implemented method of claim 1, wherein providing the alert comprises displaying, by the device, a push notification.

6. The computer-implemented method of claim 1, wherein the device is communicably connectable to the receiver via a Bluetooth Low Energy connection.

7. The computer-implemented method of claim 1, wherein the receiver is configured to receive a signal from an ingestible event marker conductively transmitted through the body of the user after ingestion of the ingestible event marker.

8. The computer-implemented method of claim 1, further comprising:
receiving, by the device, a plurality of voltage measurements at a first rate during a time period; and
receiving, by the device, the plurality of voltage measurements at a second rate after the time period.

9. The computer-implemented method of claim 8, wherein the time period begins when the reusable control module is connected to the disposable strip.

10. The computer-implemented method of claim 8, wherein the first rate is greater than the second rate.

11. A system comprising:
a receiver comprising:
a disposable strip; and
a reusable control module removably connectable to the disposable strip;
the disposable strip comprising:
an adhesive surface for attachment to a body of a user;
an electrode configured to be situated against the body of the user; and
a power source;
the reusable control module lacking its own power source and configured to be powered on when connected to the disposable strip;
the reusable control module comprising:
a voltage sensor configured to detect a voltage measurement of the power source when the reusable control module is connected to the disposable strip; and
a temperature sensor configured to detect a temperature measurement of the disposable strip when the reusable control module is connected to the disposable strip; and
a device communicably connectable to the receiver and comprising:
a processor; and
a memory coupled to the processor, the memory storing instructions that, when executed by the processor, cause the device to:
receive the voltage measurement of the power source from the voltage sensor of the reusable control module;
receive the temperature measurement of the disposable strip from the temperature sensor of the reusable control module;
normalize the voltage measurement according to the temperature measurement to generate a normalized voltage measurement;
determine whether the normalized voltage measurement falls below a voltage threshold;
count a consecutive number of normalized voltage measurements that fall below the voltage threshold;
calculate an aggregate voltage according to whether the consecutive number of normalized voltage measurements exceeds a threshold;
determine whether the calculated aggregate voltage falls below an aggregate voltage threshold; and
provide an alert according to whether the calculated aggregate voltage falls below the aggregate voltage threshold.

12. The system of claim 11, wherein the instructions, when executed by the processor, cause the device to normalize the voltage measurement by causing the device to:
apply a scaling factor corresponding to the temperature measurement to the voltage measurement.

13. The system of claim 11, wherein the instructions, when executed by the processor, cause the device to normalize the voltage measurement by causing the device to:
normalize the voltage measurement to a nominal temperature associated with one of a plurality of characterized battery voltage curves to which the voltage measurement and the temperature measurement corresponds.

14. The system of claim 11, wherein the instructions, when executed by the processor, cause the device to compute the aggregate voltage by causing the device to:
plot a curve of the voltage measurement over time; and
compute an area under the curve for a time interval.

15. The system of claim 11, wherein providing the alert comprises displaying, by the device, a push notification.

16. The system of claim 11, wherein the device is communicably connectable to the receiver via a Bluetooth Low Energy connection.

17. The system of claim 11, wherein the receiver is configured to receive a signal from an ingestible event marker conductively transmitted through the body of the user after ingestion of the ingestible event marker.

18. The system of claim 11, wherein the instructions, when executed by the processor, further cause the device to:
receive a plurality of voltage measurements at a first rate during a time period; and
receive the plurality of voltage measurements at a second rate after the time period.

19. The system of claim 18, wherein the time period begins when the reusable control module is connected to the disposable strip.

20. The system of claim 18, wherein the first rate is greater than the second rate.

* * * * *